US010576293B2

(12) United States Patent
Peterson et al.

(10) Patent No.: US 10,576,293 B2
(45) Date of Patent: Mar. 3, 2020

(54) CIRCUITS AND METHODS FOR USING A HIGH IMPEDANCE, THIN, COIN-CELL TYPE BATTERY IN AN IMPLANTABLE ELECTROACUPUNCTURE DEVICE

(71) Applicant: Valencia Technologies Corporation, Valencia, CA (US)

(72) Inventors: David K. L. Peterson, Valencia, CA (US); Jeffrey H. Greiner, Valencia, CA (US)

(73) Assignee: Valencia Technologies Corporation, Valencia, CA (US)

(*) Notice: Subject to any disclaimer, the term of this patent is extended or adjusted under 35 U.S.C. 154(b) by 101 days.

(21) Appl. No.: 15/793,913

(22) Filed: Oct. 25, 2017

(65) Prior Publication Data
US 2018/0071537 A1  Mar. 15, 2018

Related U.S. Application Data

(60) Continuation of application No. 14/805,336, filed on Jul. 21, 2015, now Pat. No. 9,827,428, which is a (Continued)

(51) Int. Cl.
*A61N 1/378* (2006.01)
*A61N 1/375* (2006.01)
(Continued)

(52) U.S. Cl.
CPC ........... *A61N 1/378* (2013.01); *A61H 39/002* (2013.01); *A61N 1/36125* (2013.01);
(Continued)

(58) Field of Classification Search
CPC .. A61N 1/378; A61N 1/3782; A61N 1/36175; A61N 1/36125; A61N 1/37205;
(Continued)

(56) References Cited

U.S. PATENT DOCUMENTS 4,031,899 A   6/1977 Renirie
4,157,720 A   6/1979 Greatbatch et al.
(Continued)

OTHER PUBLICATIONS

Cheung, "The Mechanism of Acupuncture Therapy and Clinical Case Studies", Taylor and Francis, published in London. 2001. ISBN 0-415-27254-8. The Forward, Chapters 1-3, and 5.
(Continued)

*Primary Examiner* — Christopher A Flory
*Assistant Examiner* — Minh Duc G Pham
(74) *Attorney, Agent, or Firm* — ALG Intellectual Property, LLC

(57) ABSTRACT

An implantable electroacupuncture device for treating a medical condition of a patient through application of electroacupuncture stimulation pulses to a target tissue location within the patient includes 1) a housing configured to be implanted beneath a skin surface of the patient, 2) pulse generation circuitry located within the housing and electrically coupled to at least two electrodes, the pulse generation circuitry being adapted to deliver stimulation sessions by way of the at least two electrodes to the target tissue location in accordance with a stimulation regimen, and 3) a primary battery contained within the housing and electrically coupled to the pulse generation circuitry, the primary battery having an internal impedance greater than 5 ohms and a capacity of less than 60 mAh, wherein the primary battery is the only battery that provides power to the pulse generation circuitry.

20 Claims, 21 Drawing Sheets

Related U.S. Application Data division of application No. 13/769,699, filed on Feb. 18, 2013, now Pat. No. 9,089,716, which is a continuation-in-part of application No. 13/598,582, filed on Aug. 29, 2012, now Pat. No. 8,965,511.

(60) Provisional application No. 61/609,875, filed on Mar. 12, 2012, provisional application No. 61/672,257, filed on Jul. 16, 2012, provisional application No. 61/672,661, filed on Jul. 17, 2012, provisional application No. 61/673,254, filed on Jul. 19, 2012, provisional application No. 61/674,691, filed on Jul. 23, 2012.

(51) Int. Cl.
*A61H 39/00* (2006.01)
*A61N 1/36* (2006.01)
*A61N 1/372* (2006.01)

(52) U.S. Cl.
CPC ....... *A61N 1/36175* (2013.01); *A61N 1/3756* (2013.01); *A61N 1/3782* (2013.01); *A61N 1/37205* (2013.01); A61H 2201/5005 (2013.01); A61H 2201/5035 (2013.01); A61H 2201/5038 (2013.01); A61H 2201/5097 (2013.01); A61N 1/36117 (2013.01); A61N 1/3758 (2013.01)

(58) Field of Classification Search
CPC .......... A61N 1/3756; A61N 1/3758; A61N 1/36117; A61H 2201/5008; A61H 2201/5097; A61H 2201/5035; A61H 2201/5038
USPC .......................................................... 607/59
See application file for complete search history.

(56) References Cited

U.S. PATENT DOCUMENTS

| | | | |
|---|---|---|---|
| 4,345,604 A | 8/1982 | Renirie | |
| 4,528,072 A | 7/1985 | Kurosawa et al. | |
| 4,535,784 A | 8/1985 | Rohlicek et al. | |
| 4,566,064 A | 1/1986 | Whitaker | |
| 5,195,517 A | 3/1993 | Chen | |
| 5,199,428 A | 4/1993 | Obel et al. | |
| 5,211,175 A | 5/1993 | Gleason et al. | |
| 5,250,068 A | 10/1993 | Ideguchi et al. | |
| 5,251,637 A | 10/1993 | Shalvi | |
| 5,330,515 A | 7/1994 | Rutecki et al. | |
| 5,372,605 A * | 12/1994 | Adams ................ | A61N 1/3787 607/29 |
| 5,544,656 A | 8/1996 | Pitsillides et al. | |
| 5,707,400 A | 1/1998 | Terry, Jr. et al. | |
| 5,891,181 A | 4/1999 | Zhu | |
| 6,006,134 A | 12/1999 | Hill et al. | |
| 6,178,352 B1 | 1/2001 | Gruzdowich et al. | |
| 6,393,324 B2 | 5/2002 | Gruzdowich et al. | |
| 6,522,926 B1 | 2/2003 | Kieval et al. | |
| 6,658,298 B2 | 12/2003 | Gruzdowich et al. | |
| 6,735,475 B1 | 5/2004 | Whitehurst et al. | |
| 6,839,596 B2 | 1/2005 | Nelson et al. | |
| 6,950,707 B2 | 9/2005 | Whitehurst | |
| 6,978,174 B2 | 12/2005 | Gelfand et al. | |
| 7,003,352 B1 | 2/2006 | Whitehurst | |
| 7,013,177 B1 | 3/2006 | Whitehurst et al. | |
| 7,046,499 B1 | 5/2006 | Imani et al. | |
| 7,136,701 B2 * | 11/2006 | Greatbatch ............ | A61N 1/08 607/5 |
| 7,155,279 B2 | 12/2006 | Whitehurst et al. | |
| 7,162,303 B2 | 1/2007 | Levin et al. | |
| 7,171,266 B2 | 1/2007 | Gruzdowich et al. | |
| 7,203,548 B2 | 4/2007 | Whitehurst et al. | |
| 7,292,890 B2 | 11/2007 | Whitehurst et al. | |
| 7,321,792 B1 | 1/2008 | Min et al. | |
| 7,373,204 B2 | 5/2008 | Gelfand et al. | |
| 7,440,806 B1 | 10/2008 | Whitehurst et al. | |
| 7,610,100 B2 | 10/2009 | Jaax et al. | |
| 7,620,451 B2 | 11/2009 | Demarais et al. | |
| 7,657,316 B2 | 2/2010 | Jaax et al. | |
| 7,962,219 B2 | 6/2011 | Jaax et al. | |
| 9,327,134 B2 | 5/2016 | Greiner et al. | |
| 2003/0078624 A1 | 4/2003 | Carlson et al. | |
| 2003/0078642 A1 | 4/2003 | Malaney et al. | |
| 2003/0158588 A1 | 8/2003 | Rizzo et al. | |
| 2003/0187485 A1* | 10/2003 | Sturman ................ | A61N 1/08 607/72 |
| 2003/0195583 A1 | 10/2003 | Gruzdowich et al. | |
| 2004/0088036 A1 | 5/2004 | Gilbert | |
| 2005/0107832 A1* | 5/2005 | Bernabei ................ | A61H 7/008 607/3 |
| 2005/0228460 A1 | 10/2005 | Levin et al. | |
| 2005/0234533 A1* | 10/2005 | Schulman ................ | A61N 1/05 607/115 |
| 2006/0041283 A1 | 2/2006 | Gelfand et al. | |
| 2007/0005119 A1 | 1/2007 | Crohn | |
| 2007/0219595 A1 | 9/2007 | He | |
| 2007/0255319 A1 | 11/2007 | Greenberg et al. | |
| 2007/0265680 A1 | 11/2007 | Liu | |
| 2009/0210026 A1* | 8/2009 | Solberg ............. | A61N 1/36082 607/45 |
| 2009/0292341 A1* | 11/2009 | Parramon ............ | A61N 1/3605 607/61 |
| 2010/0069992 A1 | 3/2010 | Aghassian et al. | |
| 2010/0211132 A1 | 8/2010 | Nimmagadda et al. | |
| 2010/0324624 A1 | 12/2010 | Chang | |
| 2010/0327887 A1* | 12/2010 | Denison ............... | A61B 5/0002 324/692 |
| 2011/0106220 A1 | 5/2011 | DeGiorgio et al. | |
| 2011/0112603 A1 | 5/2011 | DeGiorgio et al. | |
| 2011/0172739 A1 | 7/2011 | Mann et al. | |
| 2011/0218589 A1 | 9/2011 | DeGiorgio et al. | |
| 2011/0218590 A1 | 9/2011 | DeGiorgio et al. | |
| 2012/0022612 A1 | 1/2012 | Littlewood et al. | |
| 2012/0259390 A1 | 10/2012 | Canion | |
| 2013/0041396 A1 | 2/2013 | Ryotokuji | |

OTHER PUBLICATIONS

Li, "Neural Mechanism of Electroacupuncture's Hypotensive Effects", *Autonomic Neuroscience: Basic and Clinical* 157 (2010) 24-30.
"Acupuncture Today: Electroacupuncture", Feb. 1, 2004. Retrieved on-line Aug. 9, 2006 at http://www.acupuncturetoday.com/abc/electroacupuncture.php.
"WHO Standard Acupuncture Point Locations in the Western Pacific Region", published by *the World Health Organization (WHO), Western Pacific Region*, 2008 (updated and reprinted 2009), ISBN 978 92 9061 248 7. The Table of Contents, Forward (p. v-vi), and General Guidelines for Acupuncture Point Locations (pp. 1-21), as well as pp. 45, 64, 151, and 154.
"Acupuncture", http://en.wikipedia.org/wiki/Acupuncture.
"Electroacupuncture", http://en.wikipedia.org/wiki/Electroacupuncture.
"Delta-sigma Modulation", http://en.wikipedia.org/wiki/Delta-sigma_modulation.
Song, Kiseok "The Compact Electro-Acupuncture System for Multi-Modal Feedback Electro-Acupuncture Treatment", *34th Annual International Conference of the IEEE EMBS*, San Diego, CA, USA, Aug. 28-Sep. 1, 2012.
Non-Final Office Action received in U.S. Appl. No. 14/805,336 dated Oct. 5, 2016.
Final Office Action received in U.S. Appl. No. 14/805,336 dated Mar. 23, 2017.

* cited by examiner

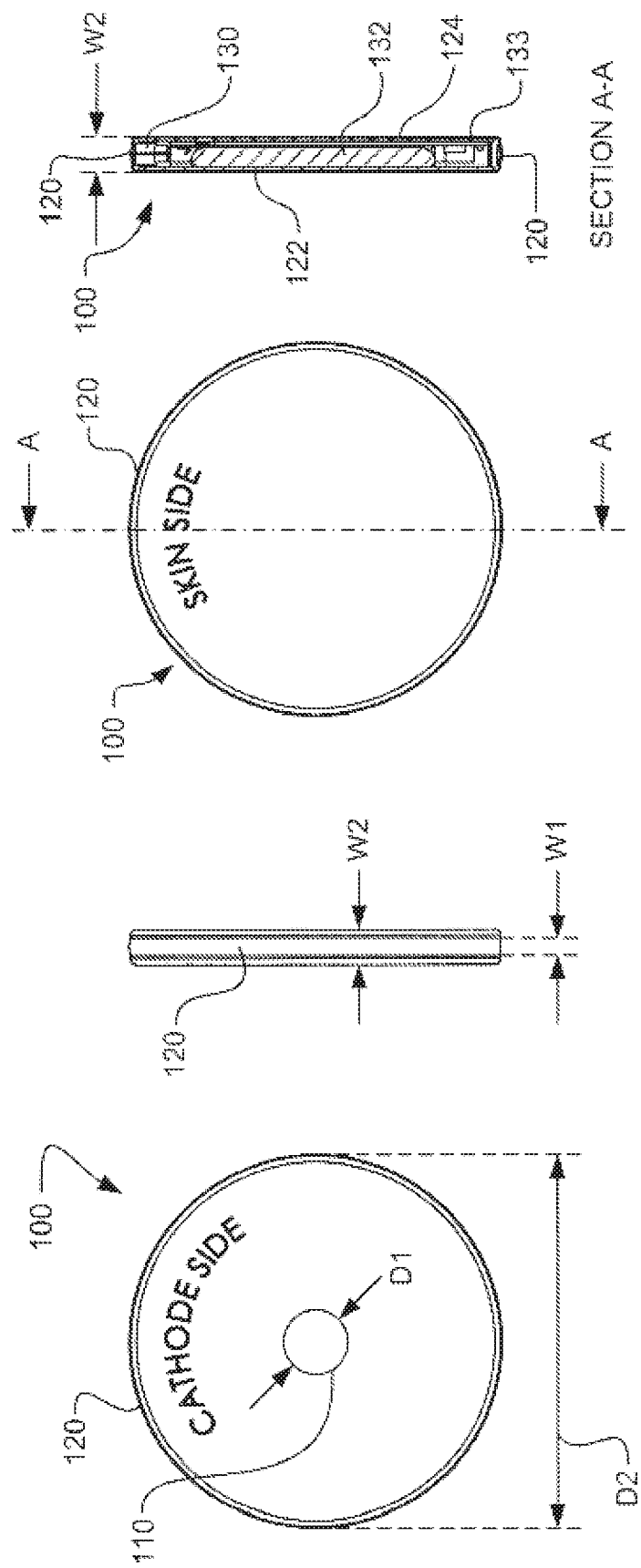

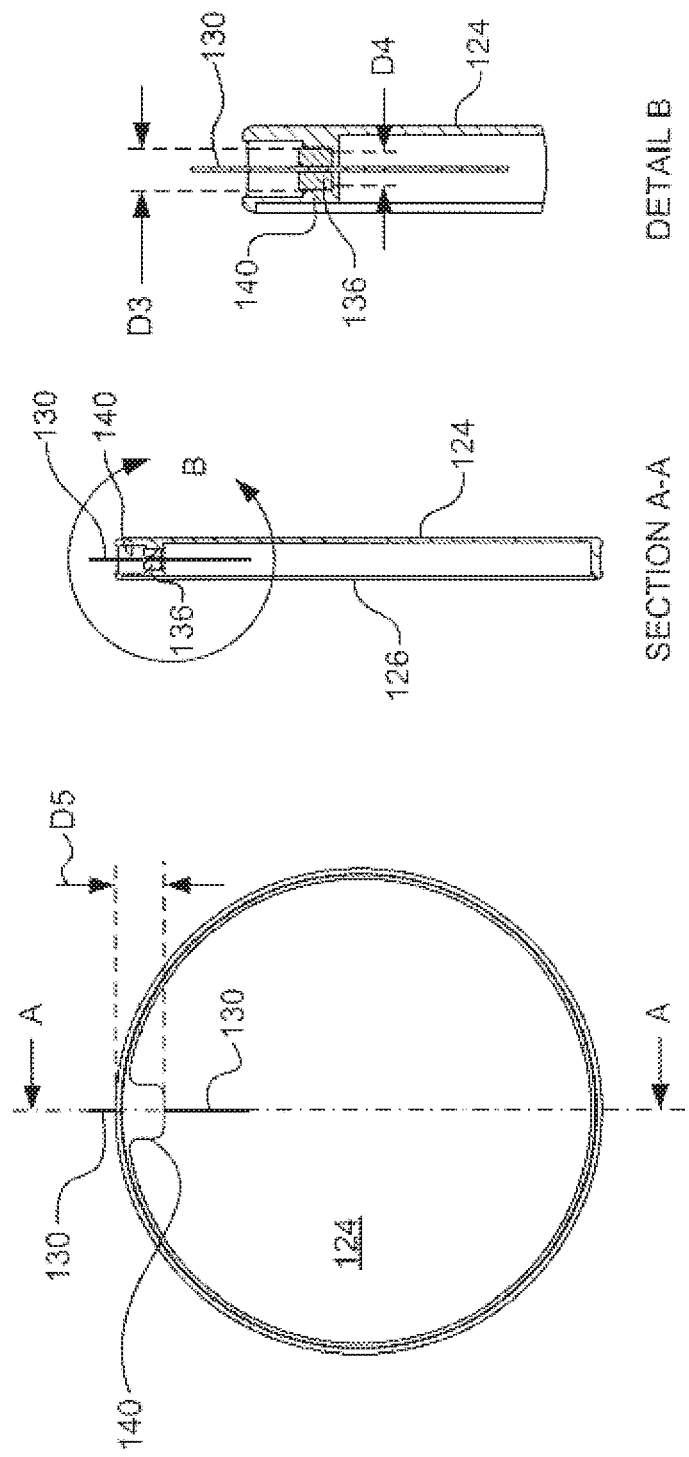

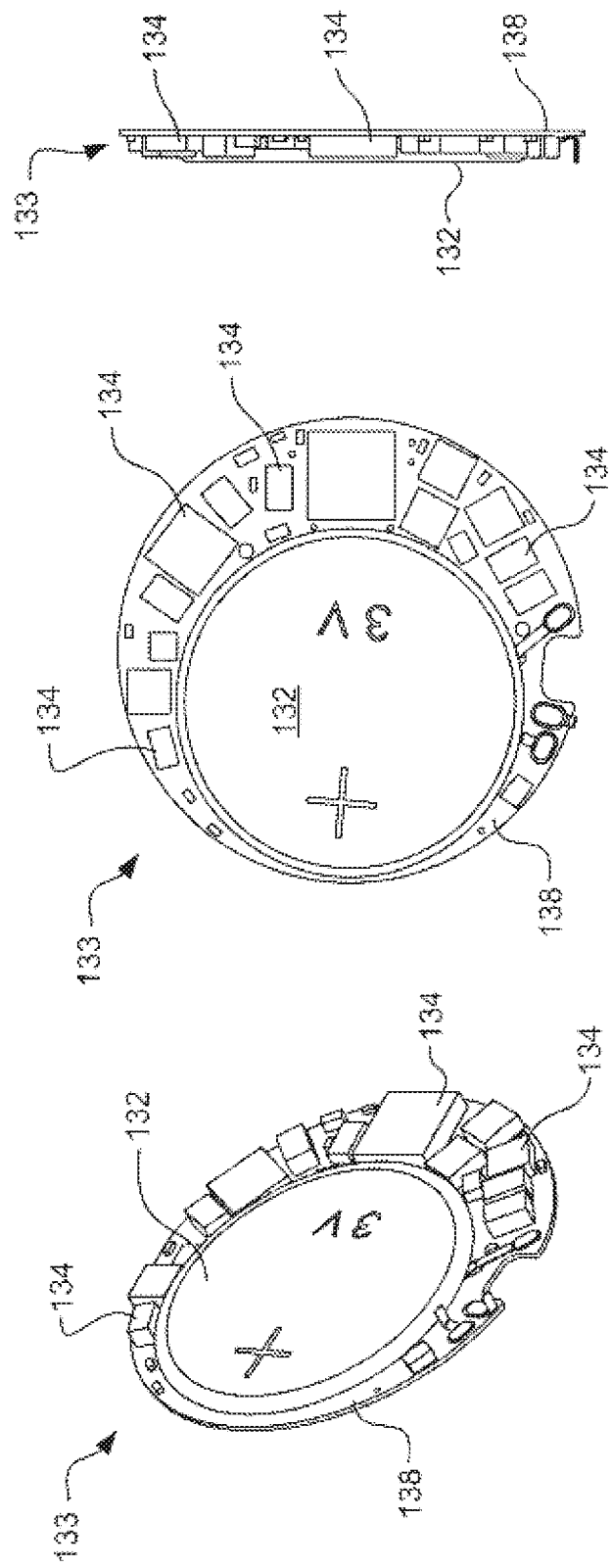

CIRCUITS AND METHODS FOR USING A HIGH IMPEDANCE, THIN, COIN-CELL TYPE BATTERY IN AN IMPLANTABLE ELECTROACUPUNCTURE DEVICE

RELATED APPLICATIONS

The present application is a continuation application of U.S. patent application Ser. No. 14/805,336, filed Jul. 21, 2015, which is a divisional application of U.S. patent application Ser. No. 13/769,699, filed Feb. 18, 2013 and issued as U.S. Pat. No. 9,089,716, which application is a continuation-in-part application of U.S. patent application Ser. No. 13/598,582, filed Aug. 29, 2012 and issued as U.S. Pat. No. 8,965,511. U.S. patent application Ser. No. 13/769, 699 also claims priority under 35 U.S.C. § 119(e) to U.S. Provisional Patent Application No. 61/609,875, filed Mar. 12, 2012; U.S. Provisional Patent Application No. 61/672, 257, filed Jul. 16, 2012; U.S. Provisional Patent Application No. 61/672,661, filed Jul. 17, 2012; U.S. Provisional Patent Application No. 61/673,254, filed Jul. 19, 2012; and U.S. Provisional Patent Application No. 61/674,691, filed Jul. 23, 2012. All of these applications are incorporated herein by reference in their respective entireties.

BACKGROUND INFORMATION

Coin-cell type batteries are known in the art. They can be used for just about any electronic device or circuit where small size is needed, e.g., because of the needed portability of the device, and power consumption demands are low.

Coin-cell type batteries are thus employed in a wide variety of hand-held electronic gadgets and controls, such as cameras, garage-door openers, remote controls, medical monitors (e.g., sensors for sensing body temperature when placed in the mouth, ear, or other body cavity), hearing aids, wristwatches, and the like. Coin-cell type batteries may also commonly be found where a tiny backup power source is needed to power a critical circuit element, such as volatile memory circuits or the system clock, within a large computer system.

Recent enhancements made to coin-cell type batteries, such as switching to a lithium-based chemistry, have increased the capacity of the coin-cell battery so that the battery can be made thinner while still providing the output capacity previously available in only larger, especially thicker, batteries. Such enhancements have allowed the devices in which the enhanced batteries are used to be made smaller than has heretofore been possible. However, the power output capacity of such batteries is still severely limited. That is, such enhanced batteries are still not capable of powering any type of electronic circuit where the instantaneous output current drawn from the battery—needed to power the circuit so that it can reliably perform its intended function—must be more than a few milliamps for more than a second or two.

The problem inherent in coin-cell type batteries, including the enhanced coin-cell batteries employing lithium-based chemistry, is that they have a relatively high output impedance, often as high as 100 to 200 ohms. This high output impedance causes the output voltage of the battery to drop below its nominal voltage value as a function of the instantaneous output current drawn from the battery as a function of ohm's law, V=IR, where V is voltage, I is current, and R is (in this instance) impedance. Thus, if the nominal output voltage of the battery is 3 volts, and if output impedance of the battery is 100 ohms, and the output current drawn from the battery is 6 milliamps (ma), then the battery voltage will drop from 3 volts to 3−(6 ma×100 ohms)=3.0−0.6=2.4 volts, or a 20% drop in the output voltage of the battery. Such a dramatic drop in battery voltage could easily cause the circuit(s) powered by the coin-cell battery to malfunction.

For an implantable medical device—where reliable operation of the device is critical for the efficacy of the device as well as the safety of the patient within whom the device is implanted—such a 20% drop in battery voltage is not acceptable. Hence, it has long been a key design constraint that batteries used in an implantable medical device must have a battery impedance that is very low, usually less than 1.0 ohm, e.g., 0.3 to 0.5 ohms.

To obtain a battery with an impedance less than 1 ohm requires a custom-made battery. Custom-made batteries having a very low impedance have thus become the "standard" for use in implantable medical devices. This is especially the case for devices that produce stimulation pulses, such as a pacemaker or a neurostimulator, where the stimulus current produced by the device must produce a stimulus pulse of sufficient intensity (e.g., where "intensity" is typically measured in current or voltage amplitude) for the stimulus pulse to achieve its intended function of stimulating muscle tissue or nerves in the area where the stimulus pulse is applied to body tissue.

Custom-made batteries having a very low impedance suitable for use in an implantable medical device are known in the art. However, such custom-made batteries tend to be quite large and very expensive. The size of the battery is dictated primarily by the basic battery chemistry and structure needed to achieve the necessary low battery impedance.

Thus, it is seen that because coin-cell batteries inherently have a high battery impedance—on the order of 100 to 200 ohms—they have never been considered for use in implantable medical devices, except perhaps extremely simple applications, such as monitoring internal body temperature, where the current demands placed on the battery are very low, e.g., less than 100 microamperes (0.1 ma).

What is needed, therefor, is electronic circuitry, and methods for operating such circuitry, that allows a small, thin, low cost, high impedance battery, such as a coin-cell type battery, to be used in an implantable medical device, such as an implantable neurostimulator.

Traditional acupuncture and acupressure has been practiced in Eastern civilizations (principally in China, but also in other Asian countries) for at least 2500 years. It is still practiced today throughout many parts of the world, including the United States and Europe. Acupuncture is an alternative medicine that treats patients by insertion and manipulation of needles in the body at selected points. See, Novak, Patricia D. et al (1995). Dorland's Pocket Medical Dictionary (25th ed.), Philadelphia: (W.B. Saunders Publisher), ISBN 0-7216-5738-9. The locations where the acupuncture needles are inserted are referred to as "acupuncture points" or simply just "acupoints". The location of acupoints in the human body has been developed over thousands of years of acupuncture practice, and maps showing the location of acupoints in the human body are readily available in acupuncture books or online. For example, see, "Acupuncture Points Map," found online at: http://www.acupuncture-healing.org/acupuncture-points-map.html. Acupoints are typically identified by various letter/number combinations, e.g., L6, S37. The maps that show the location of the acupoints may also identify what condition, illness or deficiency the particular acupoint affects when manipulation of needles inserted at the acupoint is undertaken.

References to the acupoints in the literature are not always consistent with respect to the format of the letter/number combination. Some acupoints are identified by a name only, e.g., Tongli. The same acupoint may be identified by others by the name followed with a letter/number combination placed in parenthesis, e.g., Tongli (HT5). Alternatively, the acupoint may be identified by its letter/number combination followed by its name, e.g., HT5 (Tongli). The first letter typically refers to a body organ, or other tissue location associated with, or affected by, that acupoint. However, usually only the letter is used in referring to the acupoint, but not always. Thus, for example, the acupoint ST40 is the same as acupoint Stomach 40 which is the same as ST-40 which is the same as ST 40 which is the same as Fenglong. For purposes of this patent application, unless specifically stated otherwise, all references to acupoints that use the same name, or the same first letter and the same number, and regardless of slight differences in second letters and formatting, are intended to refer to the same acupoint.

An excellent reference book that identifies all of the traditional acupoints within the human body is *WHO STANDARD ACUPUNCTURE POINT LOCATIONS IN THE WESTERN PACIFIC REGION*, published by the World Health Organization (WHO), Western Pacific Region, 2008 (updated and reprinted 2009), ISBN 978 92 9061 248 7 (hereafter "*WHO Standard Acupuncture Point Locations 2008*"). The Table of Contents, Forward (page v-vi) and General Guidelines for Acupuncture Point Locations (pages 1-21) of the *WHO Standard Acupuncture Point Locations 2008* are incorporated herein by reference. Moreover, the above-cited portions of the *WHO Standard Acupuncture Point Locations 2008* reference book may be found as Appendix D in Applicant's earlier-filed patent application, U.S. patent application Ser. No. 13/598,582, filed Aug. 29, 2012, which application, including its appendices, are also incorporated herein by reference.

As an alternative to traditional acupuncture, some have proposed applying moderate electrical stimulation at selected acupuncture points through needles that have been inserted at those points. See, e.g., http://en.wikipedia.org/wiki/Electroacupuncture. Such electrical stimulation is known as electroacupuncture (EA). According to Acupuncture Today, a trade journal for acupuncturists: "Electroacupuncture is quite similar to traditional acupuncture in that the same points are stimulated during treatment. As with traditional acupuncture, needles are inserted on specific points along the body. The needles are then attached to a device that generates continuous electric pulses using small clips. These devices are used to adjust the frequency and intensity of the impulse being delivered, depending on the condition being treated. Electroacupuncture uses two needles at a time so that the impulses can pass from one needle to the other. Several pairs of needles can be stimulated simultaneously, usually for no more than 30 minutes at a time." "Acupuncture Today: Electroacupuncture". 2004 Feb. 1 (retrieved on-line 2006 Aug. 9 at http://www.acupuncturetoday.com/abc/electroacupuncture.php).

U.S. Pat. No. 6,735,475, issued to Whitehurst et al., discloses use of an implantable miniature neurostimulator, referred to as a "microstimulator," that can be implanted into a desired tissue location and used as a therapy for headache and/or facial pain. The microstimulator has a tubular shape, with electrodes at each end.

Other patents of Whitehurst et al. teach the use of this small, microstimulator, placed in other body tissue locations, including within an opening extending through the skull into the brain, for the treatment of a wide variety of conditions, disorders and diseases. See, e.g., U.S. Pat. No. 6,950,707 (obesity and eating disorders); U.S. Pat. No. 7,003,352 (epilepsy by brain stimulation); U.S. Pat. No. 7,013,177 (pain by brain stimulation); U.S. Pat. No. 7,155,279 (movement disorders through stimulation of Vagus nerve with both electrical stimulation and drugs); U.S. Pat. No. 7,292,890 (Vagus nerve stimulation); U.S. Pat. No. 7,203,548 (cavernous nerve stimulation); U.S. Pat. No. 7,440,806 (diabetes by brain stimulation); U.S. Pat. No. 7,610,100 (osteoarthritis); and U.S. Pat. No. 7,657,316 (headache by stimulating motor cortex of brain).

Techniques for using electrical devices, including external EA devices, for stimulating peripheral nerves and other body locations for treatment of various maladies are known in the art. See, e.g., U.S. Pat. Nos. 4,535,784; 4,566,064; 5,195,517; 5,250,068; 5,251,637; 5,891,181; 6,393,324; 6,006,134; 7,171,266; and 7,171,266. The methods and devices disclosed in these patents, however, typically utilize (i) large implantable stimulators having long leads that must be tunneled through tissue over an extended distance to reach the desired stimulation site, (ii) external devices that must interface with implanted electrodes via percutaneous leads or wires passing through the skin, or (iii) inefficient and power-consuming wireless transmission schemes. Such devices and methods are still far too invasive, or are ineffective, and thus are subject to the same limitations and concerns, as are the previously described electrical stimulation devices.

From the above, it is seen that there is a need in the art for a less invasive device and technique for electroacupuncture stimulation of acupoints that does not require the continual use of needles inserted through the skin, or long insulated wires implanted or inserted into blood vessels, for the purpose of treating an illness or deficiency of a patient.

SUMMARY

One characterization of the invention described herein is a small implantable medical device using a high impedance coin-cell type battery to provide its operating power. The device generates electrical stimulation pulses, e.g., electroacupuncture (EA) pulses, and applies bursts of these pulses at a desired target tissue location of a patient, such as an acupoint, at a very low duty cycle. The device includes: (1) a small housing having an electrode configuration thereon that includes at least two electrodes, (2) a primary battery having a high battery impedance located within the housing, (3) electronic circuitry located within the housing that controls the manner in which current is drawn from the battery and which generates and delivers bursts of stimulation pulses to the patient's body tissue at the target tissue location, and (4) a sensor located within the device housing responsive to operating commands wirelessly communicated to the device from a non-implanted location. These operating commands allow limited external control of the device, such as ON/OFF and stimulation pulse amplitude adjustment.

In one embodiment, the device housing is coin-sized and -shaped, having a nominal diameter of 23 mm, and a thickness of only 2 to 3 mm.

The electronic circuitry located within the device housing includes battery control circuitry and pulse generation circuitry. The battery control circuitry is coupled to the battery and controls how much instantaneous current can be drawn from the battery, and boosts the battery voltage to a suitable voltage level needed by the pulse generation circuitry to generate bursts of stimulation pulses of a desired intensity.

The pulse generation circuitry is configured to generate stimulation pulses in accordance with a specified stimulation regimen. This stimulation regimen defines the duration and rate at which a stimulation burst is applied to the patient. The stimulation regimen requires that the stimulation burst have a duration of no more than T3 minutes and a rate of occurrence of no more than once every T4 minutes. The duty cycle of the stimulation bursts, i.e., the ratio of T3/T4, is very low, no greater than 0.05. A representative value for T3 is, e.g., 30 minutes, and a representative value for T4 is, e.g., 7 days.

The individual stimulation pulses that occur within the each stimulation burst also have a duty cycle measured relative to the period (where the "period" is the time interval equal to the inverse of the frequency or rate of the stimulation pulses) of no greater than 2%. A representative pulse width and frequency for the stimulation pulses is 0.1 milliseconds, occurring at a pulse rate of 2 Hz.

The primary battery contained within the device housing and electrically coupled to the battery control circuitry has, in one embodiment, a nominal output voltage of 3 volts, and an internal battery impedance that is at least 5 ohms, and may be as high as 150 ohms or more. Advantageously, this battery control circuitry controls the value of the instantaneous surge current that may be drawn from the battery in order to prevent any large drops in the battery output voltage. Avoiding large drops in the battery output voltage assures that the circuits within the device will continue to operate as designed without failure. Being able to use a primary battery that has a relatively high internal impedance allows the battery to be thinner, and thus allows the device to be thinner and more easily implanted. The higher internal impedance also opens the door to using relatively inexpensive commercially-available coin-cell type batteries as the primary battery within the device, thereby greatly enhancing the manufacturability of the device and significantly lowering its cost.

Another characterization of the invention described herein is that of an implantable electroacupuncture device (IEAD) adapted to generate stimulus pulses and apply them to a target tissue location of a patient when the IEAD is implanted at or near the target tissue location. Such IEAD includes: (a) an hermetically sealed case having a linear dimension in first plane no greater than about 25 mm, and a linear dimension in a second plane orthogonal to the first plane no greater than about 2.5 mm; (b) at least one anodic electrode and at least one cathodic electrode secured to or comprising an integral part of an outside surface of the hermetically sealed case, the separation between the point where the cathodic electrode is closest to the anodic electrode being at least 5 mm; (c) electronic circuitry housed within the hermetically sealed case that causes electrical stimulus pulses to be generated and applied to the at least one cathodic electrode and the at least one anodic electrode in accordance with a prescribed stimulation regime; (d) means for electrically connecting the electronic circuitry on the inside of the hermetically sealed case to the at least two electrodes on the outside of the hermetically sealed case; and (e) a primary battery on the inside of the hermetically sealed case connected to the electronic circuitry that provides the operating power for the electronic circuitry.

The primary battery employed within the IEAD has a nominal output voltage of $V_{BAT}$ volts, where $V_{BAT}$ ranges from as low 2.2 volts to as high as 3.6 volts. Also, the primary battery further has an internal impedance greater than 5 ohms.

Electronic circuitry within the IEAD includes power management circuitry that limits the amount of instantaneous current that can be drawn from the battery. This is important because otherwise the current drawn from the battery could, because of the relatively high internal impedance of the battery, cause the battery voltage, $V_{BAT}$, to drop to unacceptably low levels that would prevent the IEAD circuits from operating properly.

The electronic circuitry further controls the generation of the electrical stimulus pulses so that the stimulus pulses are applied only during a stimulation session having a duration of T3 minutes. In contrast, the time interval between stimulation sessions is T4 minutes. The time T3 is typically short, e.g., 30 minutes, whereas the time T4 is long, e.g., 1 week. The invention requires that the ratio of T3/T4 be no greater than 0.05.

Another characterization of the invention described herein is that of a method of operating an implantable electroacupuncture device (IEAD) that is powered only by a thin, coin-cell type battery having an internal impedance greater than 5 ohms, over a period of at least 2 years. The IEAD is designed to generate stimulation pulses during a stimulation session. The method comprises: (a) powering pulse generation circuitry within the IEAD with the coin-cell type battery; (b) limiting the duration of stimulation sessions during which stimulus pulses are generated to a time period that has a duty cycle of less than 0.05, where the duty cycle is the ratio of T3 to T4, where T3 is the duration of the stimulation session, and where T4 is the time interval between stimulation sessions; (c) boosting the battery voltage from the coin-cell type battery using a boost converter circuit by a factor of at least 4 in order to provide sufficient operating power to generate current stimulus pulses of up to 25 mA during a stimulation session; and (d) limiting the instantaneous current that can be drawn from the coin-cell type battery to prevent the battery voltage, $V_{BAT}$, from dropping below safe operating levels.

In one implementation of this method, the instantaneous current drawn from the battery is limited by duty cycle modulating a boost converter circuit within the IEAD between a short ON state and a long OFF state. Such duty cycle modulation can be effectuated by either (i) generating a digital control signal within a microcontroller circuit used within the IEAD, or (ii) using a boost converter circuit within the IEAD that automatically shuts down when the battery voltage drops below a prescribed threshold, but wherein other circuitry within the IEAD remains operational.

BRIEF DESCRIPTION OF THE DRAWINGS

The above and other aspects, features and advantages of the invention will be more apparent from the following more particular description thereof, presented in conjunction with the following drawings. These drawings illustrate various embodiments of the principles described herein and are part of the specification. The illustrated embodiments are merely examples and do not limit the scope of the disclosure.

FIG. 2 shows a plan view of one surface (identified in FIG. 2 as the "Cathode Side") of the IEAD housing illustrated in FIG. 1.

FIG. 2A shows a side view of the IEAD housing illustrated in FIG. 1.

FIG. 3 shows a plan view of the other side, indicated as the "Skin Side," of the IEAD housing or case illustrated in FIG. 1.

FIG. 3A is a sectional view of the IEAD of FIG. 3 taken along the line A-A of FIG. 3.

FIG. 5 is a plan view of the empty IEAD housing shown in FIG. 4.

FIG. 5A depicts a sectional view of the IEAD housing of FIG. 5 taken along the section line A-A of FIG. 5.

FIG. 5B shows an enlarged view or detail of the portion of FIG. 5A that is encircled with the line B.

FIG. 6 is a perspective view of an electronic assembly, including a battery, adapted to fit inside of the empty housing of FIG. 4 and FIG. 5.

FIGS. 6A and 6B show a plan view and side view, respectively, of the electronic assembly shown in FIG. 6.

Figure 1:
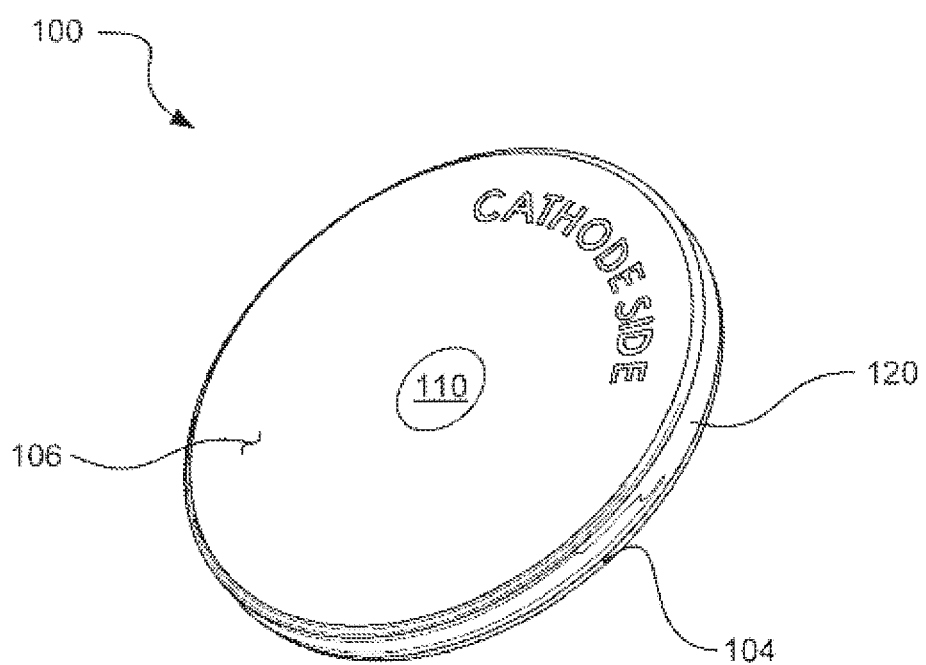
FIG. 1 is a perspective view of an Implantable Electroacupuncture Device (IEAD) made in accordance with the teachings presented herein.

Appendix A, submitted with Applicant's parent application(s) and incorporated by reference herein, illustrates some examples of alternate symmetrical electrode configurations that may be used with an IEAD of the type described herein.

Appendix B submitted with Applicant's parent application(s) and incorporated by reference herein, illustrates a few examples of non-symmetrical electrode configurations that may be used with an IEAD made in accordance with the teachings herein.

Appendix C, submitted with Applicant's parent application(s) and incorporated by reference herein, shows an example of the code used in the micro-controller IC (e.g., U2 in FIG. 13A, 14 or 14A) to control the basic operation and programming of the IEAD, e.g., to turn the IEAD ON/OFF, adjust the amplitude of the stimulus pulse, and the like, using only an external magnet as an external communication element.

Throughout the drawings, identical reference numbers designate similar, but not necessarily identical, elements.

DETAILED DESCRIPTION

Overview

Disclosed and claimed herein is an implantable, self-contained, electroacupuncture (EA) device that is powered by a small, thin, coin-cell type battery having an internal impedance of at least five ohms. While the device described is intended for, and is described for use as, an EA device, it should be noted that it may be used for other similar tissue stimulation applications. Moreover, while the preferred EA device is leadless, for some applications a short lead may be needed to correctly position the electrodes precisely at a desired stimulation site. In an exemplary embodiment, the EA device includes two electrode contacts mounted on or connected to the surface of its housing. The EA device is adapted to treat a particular disease or health condition of a patient. In one embodiment, the electrodes of the EA device are mounted on the surfaces of its housing and include a central cathode electrode on one side of the housing, and an annular anode electrode that surrounds the cathode. In another embodiment, the anode annular electrode is a ring electrode placed around the perimeter edge of a coin-shaped housing.

As indicated above, the preferred EA device is leadless. This means there are no leads or electrodes at the distal end of leads (common with most implantable electrical stimulators) that have to be positioned and anchored at a desired stimulation site. Also, because there are no leads, no tunneling through body tissue or blood vessels is required in order to provide a path for the leads to return and be connected to a tissue stimulator (also common with most electrical stimulators).

The EA device is adapted to be implanted through a very small incision, e.g., less than 2-3 cm in length, directly adjacent to a selected target stimulation site, e.g., an acupuncture site ("acupoint") known to moderate or affect an identified health condition of a patient.

The EA device is easy to implant. Also, most embodiments are symmetrical. This means that there is no way that it can be implanted incorrectly (unless the physician puts it in up-side-down, which would be difficult to do given the markings on its case). All that need be done is to cut the incision, and slide the device in place through the incision. Once the implant pocket has been prepared, it is as easy as sliding a coin into a slot. Such implantation can usually be completed in less than 10 minutes in an outpatient setting, or in a doctor's office. Only minor, local anesthesia need be used. No major or significant complications are envisioned for the implant procedure. The EA device can also be easily and quickly explanted, if needed or desired.

The EA device is self-contained. It includes a primary battery to provide its operating power. Such primary battery has a high impedance, greater than 5 ohms. In view of such high impedance, the EA device includes battery control circuitry that limits the amount of instantaneous current drawn from the primary battery to prevent excessive voltage drops in the output voltage of the battery. Such battery control circuitry carefully manages the delivery of power by the EA device so as to allow the device to perform its intended function for several years.

Once the EA device is implanted in a patient, the patient should not even know it is there, except for a slight tingling that may be felt when the device is delivering bursts of stimulus pulses during a stimulation session. Also, once implanted, the patient can just forget about it. There are no complicated user instructions that must be followed. Just turn it on. No maintenance is needed. Moreover, should the patient want to disable the EA device, i.e., turn it OFF, or change stimulus intensity, he or she can do so using, e.g., an external magnet.

The EA device can operate for several years because it is designed to be very efficient. Stimulation pulses applied by the EA device at a selected target stimulation site, e.g., a specified acupoint, are applied at a very low duty cycle in accordance with a specified stimulation regimen. The stimulation regimen applies EA stimulation during a stimulation session that lasts at least 10 minutes, typically 30 minutes, and rarely longer than 60 minutes. These stimulation sessions, however, occur at a very low duty cycle. In one preferred treatment regimen, for example, a stimulation session having a duration of 30 minutes is applied to the patient just once a week. The stimulation regimen, and the selected acupoint at which the stimulation is applied, are designed and selected to provide efficient and effective EA stimulation for the treatment of the patient's medical condition.

The EA device is, compared to most implantable medical devices, relatively easy to manufacture and uses few components. This not only enhances the reliability of the device, but keeps the manufacturing costs low, which in turn allows the device to be more affordable to the patient.

In operation, the EA device is safe to use. There are no horrific failure modes that could occur. Because it operates at a very low duty cycle (i.e., it is OFF much, much more than it is ON), it generates little heat. Even when ON, the amount of heat it generates is not much, less than 1 mW, and is readily dissipated. Should a component or circuit inside of the EA device fail, the device will simply stop working. If needed, the EA device can then be easily explanted.

A key feature included in the design of the EA device is the use of a commercially-available battery as its primary power source. A preferred commercially-available battery to use in the EA device is a small, thin, disc-shaped battery, also known as a "coin cell" battery, such as the 3 V CR1612 lithium battery available from Panasonic, or equivalents thereof. Such coin-cell batteries are quite common and readily available for use with most modern hand-held electronic devices. Such batteries come in many sizes, and employ various configurations and materials. However, insofar as the inventors or Applicant are aware, such batteries have never been used in implantable medical devices previously. This is because their internal impedance is, or has always thought to have been, much too high for such batteries to be of practical use within an implantable medical device where power consumption must be carefully monitored and managed so that the device's battery will last as long as possible. Further, because of the high internal impedance, dips in the battery output voltage (caused by any sudden surge in instantaneous battery current) may occur that could compromise the performance of the device. Additionally, the energy requirements of other active implantable therapies are far greater than can be provided by such coin cells without frequent replacement.

The EA device disclosed herein advantageously employs power-monitoring and power-managing circuits that prevent any sudden surges in battery instantaneous current, or the resulting drops in battery output voltage, from ever occurring, thereby allowing a whole family of commercially-available, very thin, high-output-impedance, relatively low capacity, small disc batteries (or "coin cells") to be used as the EA device's primary battery without compromising the EA device's performance. As a result, instead of specifying that the EA device's battery must have a high capacity, e.g., greater than 200 mAh, with an internal impedance of, e.g., less than 5 ohms, which would either require a thicker battery and/or preclude the use of commercially-available coin-cell batteries, the EA device of the present invention can readily employ a battery having a relatively low capacity, e.g., less than 60 mAh, and a high battery impedance, e.g., greater than 5 ohms.

Advantageously, the power-monitoring, power-managing, as well as the pulse generation, and control circuits used within the EA device are relatively simple in design, and may be readily fashioned from commercially-available integrated circuits (IC's) or application-specific integrated circuits (ASIC's), supplemented with discrete components, as needed. In other words, the electronic circuits employed within the EA device need not be complex nor expensive, but are simple and inexpensive, thereby making it easier to manufacture and to provide the device to patients at an affordable cost.

Definitions

As used herein, "annular", "circumferential", "circumscribing", "surrounding" or similar terms used to describe an electrode or electrode array, or electrodes or electrode arrays, (where the phrase "electrode or electrode array," or "electrodes or electrode arrays," is also referred to herein as "electrode/array," or "electrodes/arrays," respectively) refers to an electrode/array shape or configuration that surrounds or encompasses a point or object, such as another electrode, without limiting the shape of the electrode/array or electrodes/arrays to be circular or round. In other words, an "annular" electrode/array (or a "circumferential" electrode/array, or a "circumscribing" electrode/array, or a "surrounding" electrode/array), as used herein, may be many shapes, such as oval, polygonal, starry, wavy, and the like, including round or circular.

"Nominal" or "about" when used with a mechanical dimension, e.g., a nominal diameter of 23 mm, means that there is a tolerance associated with that dimension of no more than plus or minus (+/−) 5%. Thus, a dimension that is nominally 23 mm means a dimension of 23 mm+/−1.15 mm (0.05×23 mm=1.15 mm).

"Nominal" when used to specify a battery voltage is the voltage by which the battery is specified and sold. It is the voltage you expect to get from the battery under typical conditions, and it is based on the battery cell's chemistry. Most fresh batteries will produce a voltage slightly more than their nominal voltage. For example, a new nominal 3 volt lithium coin-sized battery will measure more than 3.0 volts, e.g., up to 3.6 volts under the right conditions. Since temperature affects chemical reactions, a fresh warm battery will have a greater maximum voltage than a cold one. For example, as used herein, a "nominal 3 volt" battery voltage is a voltage that may be as high as 3.6 volts when the battery is brand new, but is typically between 2.7 volts and 3.4 volts, depending upon the load applied to the battery (i.e., how much current is being drawn from the battery) when the measurement is made and how long the battery has been in use.

As explained in more detail below, an important aspect of the invention recognizes that an electroacupuncture modulation scheme, or other tissue stimulation scheme, need not be continuous, thereby allowing the implanted device to use a small, high density, power source to provide such non-continuous modulation. (Here, it should be noted that "modulation," as that phrase is used herein, is the application of electrical stimulation pulses, at low intensities, low frequencies and low duty cycles, to at least one of the target stimulation sites, e.g., an acupuncture site that has been identified as affecting a particular condition of a patient.) As a result, the device can be very small. And, because the electrodes typically form an integral part of the housing of the device, the device may thus be implanted directly at (or very near to) the desired target tissue location.

Locations Stimulated and Stimulation Paradigms/Regimens

As a function of the condition being treated, Applicant has identified one or more acupoints, or other body tissue locations, that are most responsible and most ideal for application of bursts of stimulation pulses that treat an identified condition. Such identified tissue locations are targets for where the stimulation pulses are to be applied. For purposes of the invention claimed herein, the target locations where the stimulus pulses are applied are not critical. Instead, what is critical is how a small, thin, coin-cell type battery is able to be employed and controlled so as to generate and deliver stimulus pulses to the target tissue locations with sufficient intensity and continuity to achieve a desired result.

Applicant has further identified a frequency range as low as 1 Hz and as high as 15 Hz as an ideal stimulation frequency to use when stimulus pulses are applied for many applications. The exact frequency used, of course, may and will often vary as a function of the condition being treated. Further, the frequency employed need not always be fixed, or constant, but may vary, or gradually sweep from one frequency to another, and back again, over time. It should also be emphasized that the "frequency" being described here, is the frequency of the stimulus pulses that are applied to the target tissue location when stimulus pulses are being applied. A key aspect of the invention is that such stimulus pulses are not applied continuously, but are only applied during a stimulation session, and such stimulation session is only enabled infrequently, or at a low duty cycle. For example, a stimulation session having a duration of, e.g., 30 minutes, during which stimulus pulses (having a narrow pulse width of, e.g., 0.5 to 2 milliseconds) are applied at a frequency of 1 Hz, may only be enabled, or turned ON, once every week. Moreover, even during a stimulation session, it should be noted that the stimulus pulses need not always be applied continuously, but could be applied in bursts of stimulus pulses, e.g., a 3-5 minute burst of stimulus pulses could be applied, followed by a 3-10 minute duration of no stimulus pulses, followed by another 3-5 minute burst of stimulus pulses, followed by another period of no stimulus pulses, and so on, throughout the duration of the stimulation session (which stimulation session could be as long as, e.g., 60 to 80 minutes, or as short as 10-15 minutes).

Mechanical Design

Turning to FIG. 1, a preferred configuration of a small, implantable, electroacupuncture device will next be described. As seen in FIG. 1, a preferred implantable electroacupuncture device (IEAD) 100 is shown in perspective view. Such device is designed to be used to treat a disease, deficiency, or other medical condition of a patient. The IEAD 100 may also sometimes be referred to as an implantable electroacupuncture stimulator (IEAS). As seen in FIG. 1, the IEAD 100 has the appearance of a disc or coin, having a front side 106 (which is also labeled as the "Cathode Side") 106, a back side (also referred to as the "Skin Side")102 (which skin side is not visible in FIG. 1) and an edge side 104.

As used herein, the "front" side of the IEAD 100 is the side that is positioned so as to face the target stimulation point (e.g., the desired acupoint) where EA stimulation is to be applied when the IEAD is implanted. The "back" side is the side opposite the front side and is the farthest away from the target stimulation point when the IEAD is implanted, and is usually the side closest to the patient's skin. The "edge" of the IEAD is the side that connects or joins the front side to the back side. In FIG. 1, the IEAD 100 is oriented to show the front side 102 and a portion of the edge side 104.

Many of the features associated with the mechanical design of the IEAD 100 shown in FIG. 1 are the subject of a prior U.S. Provisional Patent Application, entitled "Radial Feed-Through Packaging for An Implantable Electroacupuncture Device", Application No. 61/676,275, filed 26 Jul. 2012, which application is incorporated here by reference.

It should be noted here that throughout this application, the terms IEAD 100, IEAD housing 100, bottom case 124, can 124, or IEAD case 124, or similar terms, are used to describe the housing structure of the EA device. In some instances it may appear these terms are used interchangeably. However, the context should dictate what is meant by these terms. As the drawings illustrate, particularly FIG. 7, there is a bottom case 124 that comprises the "can" or "container" wherein the components of the IEAD 100 are first placed and assembled during manufacture of the IEAD 100. When all of the components are assembled and placed within the bottom case 124, a cover plate 122 is welded to the bottom case 124 to form the hermetically-sealed housing of the IEAD. The cathode electrode 110 is attached to the outside of the bottom case 124 (which is the front side 102 of the device), and the ring anode electrode 120 is attached, along with its insulating layer 129, around the perimeter edge 104 of the bottom case 124. Finally, a layer of silicone molding 125 covers the IEAD housing except for the outside surfaces of the anode ring electrode and the cathode electrode.

Figure 7:
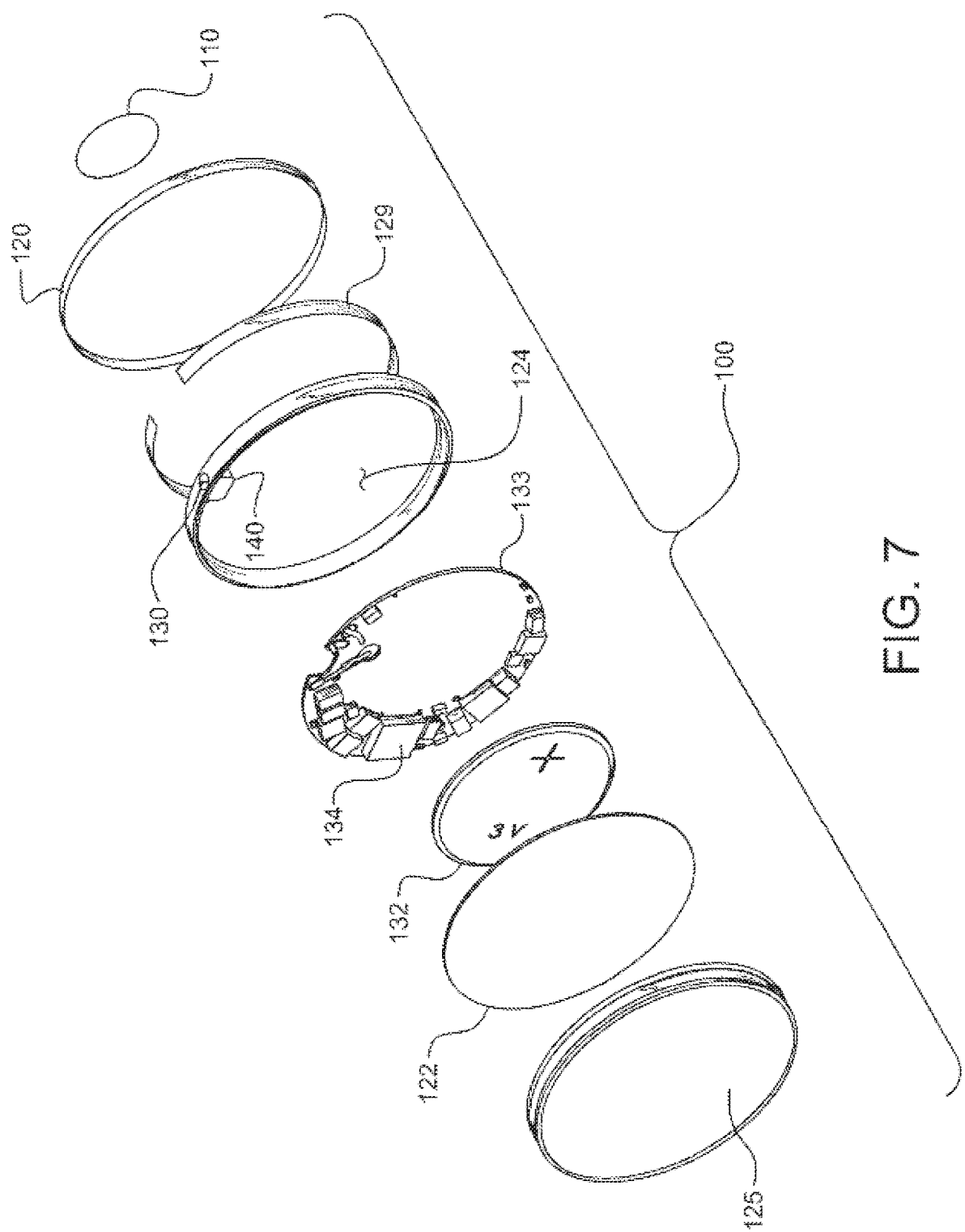
FIG. 7 is an exploded view of the IEAD assembly, illustrating its constituent parts.

The embodiment of the IEAD 100 shown in FIG. 1 utilizes two electrodes, a cathode electrode 110 that is centrally positioned on the front side 102 of the IEAD 100, and an anode electrode 120. The anode electrode 120 is a ring electrode that fits around the perimeter edge 104 of the IEAD 100. Not visible in FIG. 1, but which is described hereinafter in connection with the description of FIG. 7, is a layer of insulating material 129 that electrically insulates the anode ring electrode 120 from the perimeter edge 104 of the housing or case 124.

Not visible in FIG. 1, but a key feature of the mechanical design of the IEAD 100, is the manner in which an electrical connection is established between the ring electrode 120 and electronic circuitry carried inside of the IEAD 100. This electrical connection is established using a radial feed-through pin that fits within a recess formed in a segment of the edge of the case 124, as explained more fully below in connection with the description of FIGS. 5, 5A, 5B and 7.

In contrast to the feed-through pin that establishes electrical contact with the anode electrode, electrical connection with the cathode electrode 110 is established simply by forming or attaching the cathode electrode 110 to the front surface 102 of the IEAD case 124. In order to prevent the entire case 124 from functioning as the cathode (which is done to better control the electric fields established between the anode and cathode electrodes), the entire IEAD housing is covered in a layer of silicone molding 125 (see FIG. 7), except for the outside surface of the anode ring electrode 120 and the cathode electrode 110.

The advantage of using a central cathode electrode and a ring anode electrode is described in U.S. Provisional Patent Application No. 61/672,257, filed 6 Mar. 2012, entitled "Electrode Configuration for Implantable Electroacupuncture Device", which application is incorporated herein by reference. One significant advantage of this electrode configuration is that it is symmetrical. That is, when implanted, the surgeon or other medical personnel performing the implant procedure, need only assure that the cathode side of the IEAD 100, which (for the embodiment shown in FIGS. 1-7) is the front side of the device, faces the target tissue location that is to be stimulated. In addition, the IEAD must be implanted over the desired acupoint, or other tissue location, that is intended to receive the electroacupuncture (EA) stimulation. The orientation of the IEAD 100 is otherwise not important.

Figure 1A:
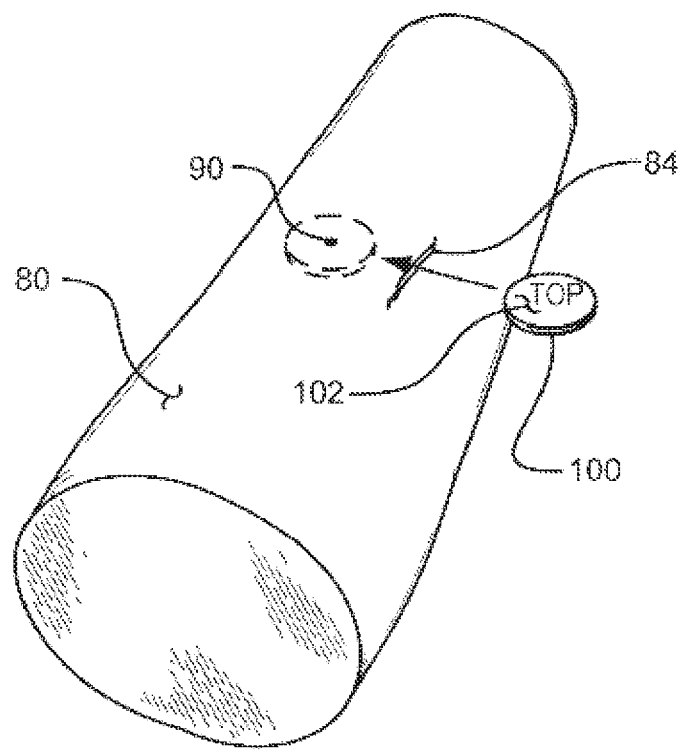
FIG. 1A illustrates the location of an exemplary target tissue stimulation site, e.g., an acupoint, whereat the IEAD of FIG. 1 may be implanted for the treatment of a particular disease or condition.

FIG. 1A illustrates illustrates the location of an exemplary target stimulation acupoint, e.g. acupoint PC6 located on the patient's wrist, whereat the IEAD of FIG. 1 may be implanted for the treatment of a particular disease or condition of the patient, e.g., hypertension. Such location is representative of a wide variety of acupoints, or other target tissue locations, whereat the IEAD of FIG. 1 could be implanted.

Figure 1B:
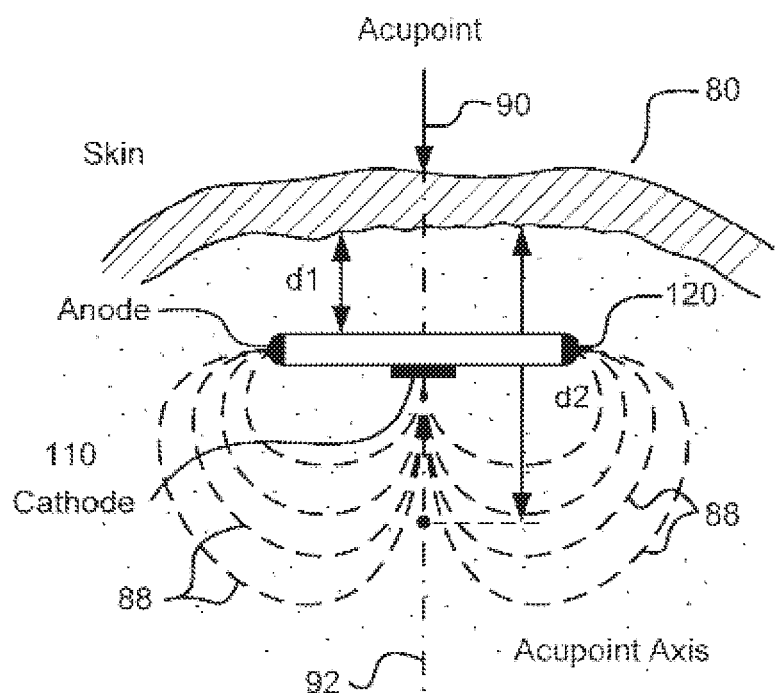
FIG. 1B shows a sectional view of an IEAD implanted at a selected target stimulation site, and illustrates the electric field gradient lines created when an electroacupuncture (EA) pulse is applied to the tissue through the central electrode and ring electrode attached to the bottom surface and perimeter edge, respectively, of the IEAD housing.

An implanted IEAD 100 is illustrated generally in FIG. 1B. Shown in FIG. 1B is a sectional view of a limb 80 of the patient wherein an acupoint 90 (e.g., acupoint ST40) has been identified that is to receive acupuncture treatment (in this case electroacupuncture treatment). An incision (not shown in FIG. 1B) is made into the limb 80 a short distance, e.g., 10-15 mm, away from the acupoint 90. A slot (parallel to the limb) is formed at the incision by lifting the skin closest to the acupoint up at the incision. As necessary, the surgeon may form a pocket under the skin at the acupoint location. The IEAD 100, with its top side 102 being closest to the skin (and thus also referred to as the "Skin Side"), is then slid through the slot 84 into the pocket so that the center of the IEAD is located under the acupoint 90 on the skin surface. This implantation process is as easy as inserting a coin into a slot. With the IEAD 100 in place, the incision is sewn or otherwise closed, leaving the IEAD 100 under the skin 80 at the location of the acupoint 90 where electroacupuncture (EA) stimulation is desired.

In this regard, it should be noted that while the target stimulation point is generally identified by an "acupoint," which is typically shown in drawings and diagrams as residing on the surface of the skin, the surface of the skin is not the actual target stimulation point. Rather, whether such stimulation comprises manual manipulation of a needle inserted through the skin at the location on the skin surface identified as an "acupoint", or whether such stimulation comprises electrical stimulation applied through an electrical field oriented to cause stimulation current to flow through the tissue at a prescribed depth below the acupoint location on the skin surface, the actual target tissue point to be stimulated is located beneath the skin at a depth d2 that varies depending on the particular acupoint location. When stimulation is applied at the target tissue point, such stimulation is effective at treating a selected condition of the patient, e.g., high cholesterol, because there is something in the tissue at that location, or near that location, such as a nerve, a tendon, a muscle, or other type of tissue, that responds to the applied stimulation in a manner that contributes favorably to the treatment of the condition experienced by the patient.

FIG. 1B illustrates a sectional view of the IEAD 100 implanted so as to be centrally located under the skin at the selected acupoint 90, and over the acupoint axis line 92. Usually, for most patients, the IEAD 100 is implanted at a depth d1 of approximately 2-4 mm under the skin. The top (skin) side 102 of the IEAD is nearest to the skin 80 of the patient. The bottom (cathode) side 106 of the IEAD, which is the side on which the central cathode electrode 110 resides, is farthest from the skin. Because the cathode electrode 110 is centered on the bottom of the IEAD, and because the IEAD 100 is implanted so as to be centered under the location on the skin where the acupoint 90 is located, the cathode 110 is also centered over the acupoint axis line 92.

FIG. 1B further illustrates the electric field gradient lines 88 that are created in the body tissue 86 surrounding the acupoint 90 and the acupoint axis line 92. (Note: for purposes herein, when reference is made to providing EA stimulation at a specified acupoint, it is understood that the EA stimulation is provided at a depth of approximately d2 below the location on the skin surface where the acupoint is indicated as being located.) As seen in FIG. 1B, the electric field gradient lines are strongest along a line that coincides with, or is near to, the acupoint axis line 92. It is thus seen that one of the main advantages of using a symmetrical electrode configuration that includes a centrally located electrode surrounded by an annular electrode is that the precise orientation of the IEAD within its implant location is not important. So long as one electrode is centered over the desired target location, and the other electrode surrounds the first electrode (e.g., as an annular electrode), a strong electric field gradient is created that is aligned with the acupoint axis line. This causes the EA stimulation current to flow along (or very near) the acupoint axis line 92, and will result in the desired EA stimulation in the tissue at a depth d2 below the acupoint location indicated on the skin.

FIG. 2 shows a plan view of the "front" (or "cathode") side 106 of the IEAD 100. As seen in FIG. 2, the cathode electrode 110 appears as a circular electrode, centered on the front side, having a diameter D1. The IEAD housing has a diameter D2 and an overall thickness or width W2. For the preferred embodiment shown in these figures, D1 is about 4 mm, D2 is about 23 mm and W2 is a little over 2 mm (2.2 mm).

FIG. 2A shows a side view of the IEAD 100. The ring anode electrode 120, best seen in FIG. 2A, has a width W1 of about 1.0 mm, or approximately ½ of the width W2 of the IEAD.

FIG. 3 shows a plan view of the "back" (or "skin") side of the IEAD 100. As will be evident from subsequent figure descriptions, e.g., FIGS. 5A and 5B, the back side of the IEAD 100 comprises a cover plate 122 that is welded in place once the bottom case 124 has all of the electronic circuitry, and other components, placed inside of the housing.

FIG. 3A is a sectional view of the IEAD 100 of FIG. 1 taken along the line A-A of FIG. 3. Visible in this sectional view is the feed-through pin 130, including the distal end of the feed-through pin 130 attached to the ring anode electrode 120. Also visible in this section view is an electronic assembly 133 on which various electronic components are mounted, including a disc-shaped battery 132. FIG. 3A further illustrates how the cover plate 122 is welded, or otherwise bonded, to the bottom case 124 in order to form the hermetically-sealed IEAD housing 100.

Figure 4:
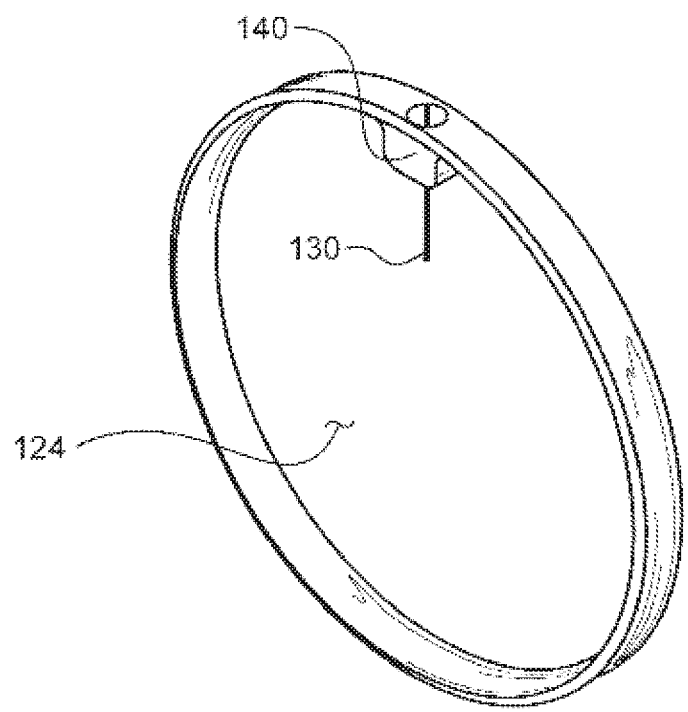
FIG. 4 is a perspective view of the IEAD housing, including a feed-through pin, before the electronic components are placed therein, and before being sealed with a cover plate.

FIG. 4 shows a perspective view of the IEAD case 124, including the feed-through pin 130, before the electronic components are placed therein, and before being sealed with the "skin side" cover plate 122. The case 124 is similar to a shallow "can" without a lid, having a short side wall around its perimeter. Alternatively, the case 124 may be viewed as a short cylinder, closed at one end but open at the other. (Note, in the medical device industry the housing of an implanted device is often referred to as a "can".) The feed-through pin 130 passes through a segment of the wall of the case 124 that is at the bottom of a recess 140 formed in the wall. The use of this recess 140 to hold the feed-through pin 130 is a key feature of the invention because it keeps the temperature-sensitive portions of the feed-through assembly (those portions that could be damaged by excessive heat) away from the thermal shock and residual weld stress inflicted upon the case 124 when the cover plate 122 is welded thereto.

Figure 4A:
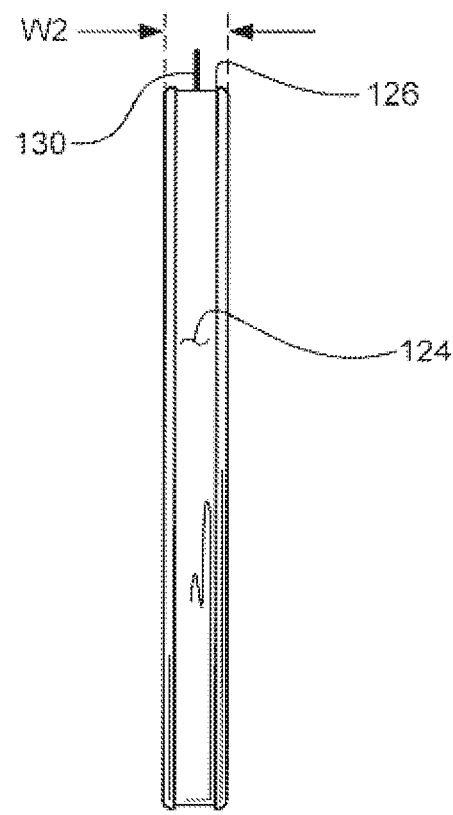
FIG. 4A is a side view of the IEAD housing of FIG. 4.

FIG. 4A is a side view of the IEAD case 124, and shows an annular rim 126 formed on both sides of the case 124. The ring anode electrode 120 fits between these rims 126 once the ring electrode 120 is positioned around the edge of the case 124. (This ring electrode 120 is, for most configurations, used as an anode electrode. Hence, the ring electrode 120 may sometimes be referred to herein as a ring anode electrode. However, it is noted that the ring electrode could also be employed as a cathode electrode, if desired.) A silicone insulator layer 129 (see FIG. 7) is placed between the backside of the ring anode electrode 120 and the perimeter edge of the case 124 where the ring anode electrode 120 is placed around the edge of the case 124.

FIG. 5 shows a plan view of the empty IEAD case 124 shown in the perspective view of FIG. 4. An outline of the recess cavity 140 is also seen in FIG. 5, as is the feed-through pin 130. A bottom edge of the recess cavity 140 is located a distance D5 radially inward from the edge of the case 124. In one embodiment, the distance D5 is between about 2.0 to 2.5 mm. The feed-through pin 130, which is just a piece of solid wire, is shown in FIG. 5 extending radially outward from the case 124 above the recess cavity 140 and radially inward from the recess cavity towards the center of the case 124. The length of this feed-through pin 130 is trimmed, as needed, when a distal end (extending above the recess) is connected (welded) to the anode ring electrode 120 (passing through a hole in the ring electrode 120 prior to welding) and when a proximal end of the feed-through pin 130 is connected to an output terminal of the electronic assembly 133.

FIG. 5A depicts a sectional view of the IEAD housing 124 of FIG. 5 taken along the section line A-A of FIG. 5. FIG. 5B shows an enlarged view or detail of the portion of FIG. 5A that is encircled with the line B. Referring to FIGS. 5A and 5B jointly, it is seen that the feed-through pin 130 is embedded within an insulator material 136, which insulating material 136 has a diameter of D3. The feed-through pin assembly (which pin assembly comprises the combination of the pin 130 embedded into the insulator material 136) resides on a shoulder around an opening or hole formed in the bottom of the recess 140 having a diameter D4. For the embodiment shown in FIGS. 5A and 5B, the diameter D3 is 0.95-0.07 mm, where the −0.07 mm is a tolerance. (Thus, with the tolerance considered, the diameter D3 may range from 0.88 mm to 0.95 mm) The diameter D4 is 0.80 mm with a tolerance of −0.06 mm. (Thus, with the tolerance considered, the diameter D4 could range from 0.74 mm to 0.80 mm).

The feed-through pin 130 is preferably made of pure platinum 99.95%. A preferred material for the insulator material 136 is Ruby or alumina. The IEAD case 124, and the cover 122, are preferably made from titanium. The feed-through assembly, including the feed-through pin 130, ruby/alumina insulator 136 and the case 124 are hermetically sealed as a unit by gold brazing. Alternatively, active metal brazing can be used. (Active metal brazing is a form of brazing which allows metal to be joined to ceramic without metallization.)

The hermeticity of the sealed IEAD housing is tested using a helium leak test, as is common in the medical device industry. The helium leak rate should not exceed $1 \times 10^{-9}$ STD cc/sec at 1 atm pressure. Other tests are performed to verify the case-to-pin resistance (which should be at least $15 \times 10^6$ Ohms at 100 volts DC), the avoidance of dielectric breakdown or flashover between the pin and the case 124 at 400 volts AC RMS at 60 Hz and thermal shock.

One important advantage provided by the feed-through assembly shown in FIGS. 4A, 5, 5A and 5B is that the feed-through assembly made from the feed-through pin 130, the ruby insulator 136 and the recess cavity 140 (formed in the case material 124) may be fabricated and assembled before any other components of the IEAD 100 are placed inside of the IEAD case 124. This advantage greatly facilitates the manufacture of the IEAD device.

Turning next to FIG. 6, there is shown a perspective view of an electronic assembly 133. The electronic assembly 133 includes a multi-layer printed circuit (pc) board 138, or equivalent mounting structure, on which a battery 132 and various electronic components 134 are mounted. This assembly is adapted to fit inside of the empty bottom housing 124 of FIG. 4 and FIG. 5.

FIGS. 6A and 6B show a plan view and side view, respectively, of the electronic assembly 133 shown in FIG. 6. The electronic components are assembled and connected together so as to perform the circuit functions needed for the IEAD 100 to perform its intended functions. These circuit functions are explained in more detail below under the sub-heading "Electrical Design". Additional details associated with these functions may also be found in many of the co-pending patent applications referenced above.

FIG. 7 shows an exploded view of the complete IEAD 100, illustrating its main constituent parts. As seen in FIG. 7, the IEAD 100 includes, starting on the right and going left, a cathode electrode 110, a ring anode electrode 120, an insulating layer 129, the bottom case 124 (the "can" portion of the IEAD housing, and which includes the feed-through pin 130 which passes through an opening in the bottom of the recess 140 formed as part of the case, but wherein the feed-through pin 130 is insulated and does not make electrical contact with the metal case 124 by the ruby insulator 136), the electronic assembly 133 (which includes the battery 132 and various electronic components 134 mounted on a pc board 138) and the cover plate 122. The cover plate 122 is welded to the edge of the bottom case 124 using laser beam welding, or some equivalent process, as one of the final steps in the assembly process.

Other components included in the IEAD assembly, but not necessarily shown or identified in FIG. 7, include adhesive patches for bonding the battery 132 to the pc board 138 of the electronic assembly 133, and for bonding the electronic assembly 133 to the inside of the bottom of the case 124. To prevent high temperature exposure of the battery 132 during the assembly process, conductive epoxy is used to connect a battery terminal to the pc board 138. Because the curing temperature of conductive epoxy is 125° C., the following process is used: (a) first cure the conductive epoxy of a battery terminal ribbon to the pc board without the battery, (b) then glue the battery to the pc board using room temperature cure silicone, and (c) laser tack weld the connecting ribbon to the battery.

Also not shown in FIG. 7 is the manner of connecting the proximal end of the feed-through pin 130 to the pc board 138, and connecting a pc board ground pad to the case 124. A preferred method of making these connections is to use conductive epoxy and conductive ribbons, although other connection methods known in the art may also be used.

Further shown in FIG. 7 is a layer of silicon molding 125 that is used to cover all surfaces of the entire IEAD 100 except for the anode ring electrode 120 and the circular cathode electrode 110. An overmolding process is used to accomplish this, although overmolding using silicone LSR 70 (curing temperature of 120° C.) with an injection molding process cannot be used. Overmolding processes that may be used include: (a) molding a silicone jacket and gluing the jacket onto the case using room temperature cure silicone (RTV) inside of a mold, and curing at room temperature; (b) injecting room temperature cure silicone in a PEEK or Teflon® mold (silicone will not stick to the Teflon® or PEEK material); or (c) dip coating the IEAD 100 in room temperature cure silicone while masking the electrode surfaces that are not to be coated. (Note: PEEK is a well known semicrystalline thermoplastic with excellent mechanical and chemical resistance properties that are retained at high temperatures.)

When assembled, the insulating layer 129 is positioned underneath the ring anode electrode 120 so that the anode electrode does not short to the case 124. The only electrical connection made to the anode electrode 120 is through the distal tip of the feed-through pin 130. The electrical contact with the cathode electrode 110 is made through the case 124. However, because the entire IEAD is coated with a layer of silicone molding 125, except for the anode ring electrode 120 and the circular cathode electrode 110, all stimulation current generated by the IEAD 100 must flow between the exposed surfaces of the anode and cathode.

It is noted that while the preferred configuration described herein uses a ring anode electrode 120 placed around the edges of the IEAD housing, and a circular cathode electrode 110 placed in the center of the cathode side of the IEAD case 124, such an arrangement could be reversed, i.e., the ring electrode could be the cathode, and the circular electrode could be the anode.

Moreover, the location and shape of the electrodes may be configured differently than is shown in the one preferred embodiment described above in connection with FIGS. 1, and 2-7. For example, the ring anode electrode 120 need not be placed around the perimeter of the device, but such electrode may be a flat circumferential electrode that assumes different shapes (e.g., round or oval) that is placed on the front or back surface of the IEAD so as to surround the central electrode. Further, for some embodiments, the surfaces of the anode and cathode electrodes may have convex surfaces.

It is also noted that while one preferred embodiment has been disclosed herein that incorporates a round, or short cylindrical-shaped housing, also referred to as a coin-shaped housing, the invention does not require that the case 124 (which may also be referred to as a "container"), and its associated cover plate 122, be round. The case could just as easily be an oval-shaped, rectangular-shaped (e.g., square with smooth corners), polygonal-shaped (e.g., hexagon-, octagon-, pentagon-shaped), button-shaped (with convex top or bottom for a smoother profile) device. Any of these alternate shapes, or others, would still permit the basic principles of the invention to be used to provide a robust, compact, thin, case to house the electronic circuitry and power source used by the invention; as well as to help protect a feed-through assembly from being exposed to excessive heat during assembly, and to allow the thin device to provide the benefits described herein related to its manufacture, implantation and use. For example, as long as the device remains relatively thin, e.g., no more than about 2-3 mm, and does not have a maximum linear dimension greater than about 25 mm, then the device can be readily implanted in a pocket over the tissue area where the selected acupuoint(s) is located. As long as there is a recess in the wall around the perimeter of the case wherein the feed-through assembly may be mounted, which recess effectively moves the wall or edge of the case inwardly into the housing a safe thermal distance, as well as a safe residual weld stress distance, from the perimeter wall where a hermetically-sealed weld occurs, the principles of the invention apply.

Further, it should be noted that while the preferred configuration of the IEAD described herein utilizes a central electrode on one of its surfaces that is round, having a diameter of nominally 4 mm, such central electrode need not necessarily be round. It could be oval shaped, polygonal-shaped, or shaped otherwise, in which case its size is best defined by its maximum width, which will generally be no greater than about 7 mm.

Finally, it is noted that the electrode arrangement may be modified somewhat, and the desired attributes of the invention may still be achieved. For example, as indicated previously, one preferred electrode configuration for use with the invention utilizes a symmetrical electrode configuration, e.g., an annular electrode of a first polarity that surrounds a central electrode of a second polarity. Such a symmetrical electrode configuration makes the implantable electroacupuncture device (IEAD) relatively immune to being implanted in an improper orientation relative to the body tissue at the selected acupoint(s) that is being stimulated. However, an electrode configuration that is not symmetrical may still be used and many of the therapeutic effects of the invention may still be achieved. For example, two spaced-apart electrodes on a front surface of the housing, one of a first polarity, and a second of a second polarity, could still, when oriented properly with respect to a selected acupoint tissue location, provide some desired therapeutic results.

Figure 7A:
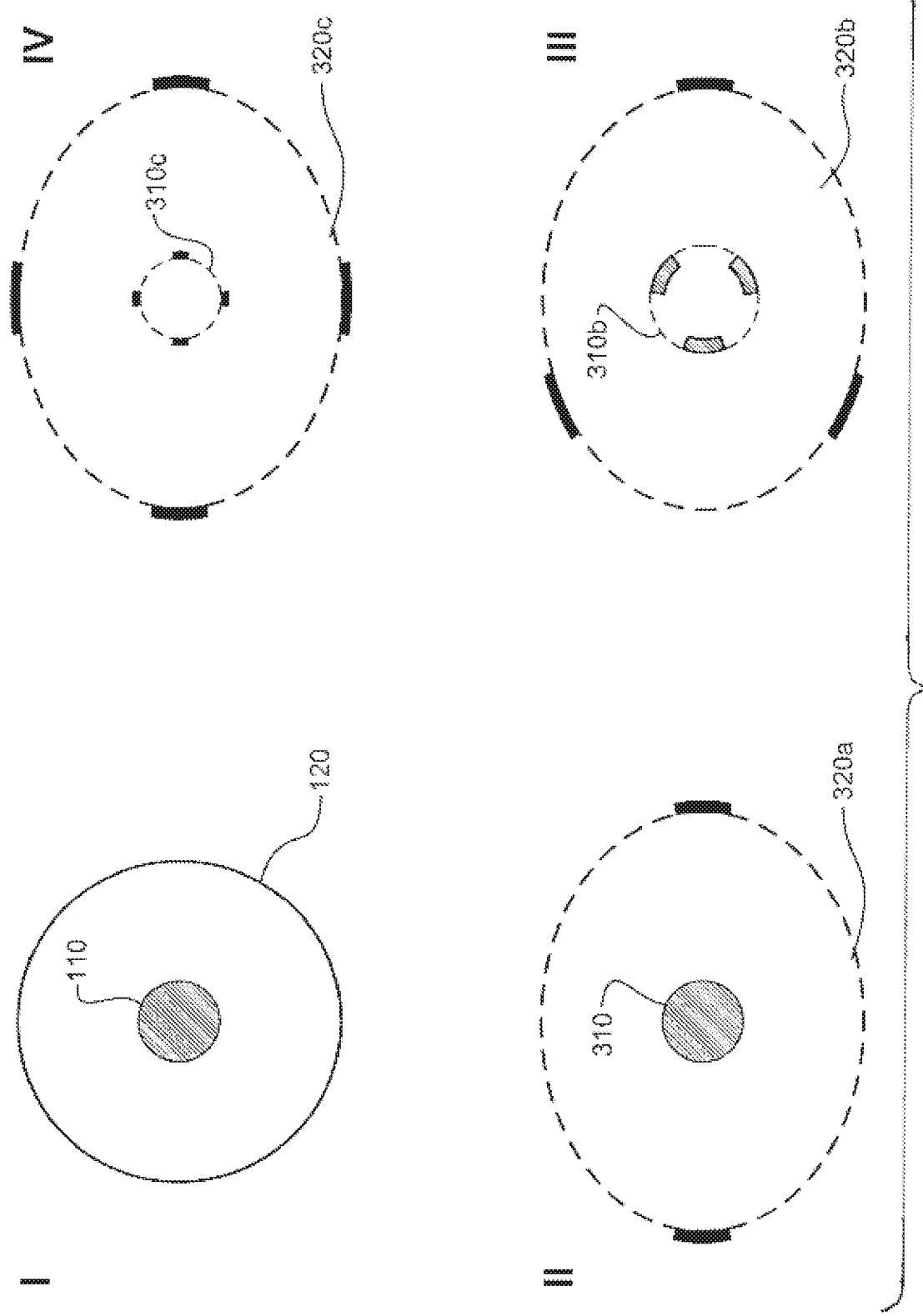
FIG. 7A schematically illustrates a few alternative electrode configurations that may be used with the invention.

FIG. 7A schematically illustrates a few alternative electrode configurations that may be used with the invention. The electrode configuration schematically shown in the upper left corner of FIG. 7A, identified as "I", schematically illustrates one central electrode 110 surrounded by a single round ring electrode 120. This is one of the preferred electrode configurations that has been described previously in connection, e.g., with the description of FIGS. 1, 1A, 1B and 7, and is presented in FIG. 7A for reference and comparative purposes.

In the lower left corner of FIG. 7A, identified as "II", an electrode/array configuration is schematically illustrated that has a central electrode 310 of a first polarity surrounded by an oval-shaped electrode array 320a of two electrodes of a second polarity. (This oval-shaped array 320a could also be round.) When the two electrodes (of the same polarity) in the electrode array 320a are properly aligned with the body tissue being stimulated, e.g., aligned with a nerve underlying the desired acupoint, then such electrode configuration can stimulate the body tissue (e.g., the underlying nerve) at or near the desired acupoint(s) with the same, or almost the same, efficacy as can the electrode configuration I (upper right corner of FIG. 7A).

Note, as has already been described above, the phrase "electrode or electrode array," or "electrodes or electrode arrays," may also be referred to herein as "electrode/array" or "electrodes/arrays," respectively. For the ease of explanation, when an electrode array is referred to herein that comprises a plurality (two or more) of individual electrodes of the same polarity, the individual electrodes of the same polarity within the electrode array may also be referred to as "individual electrodes", "segments" of the electrode array, "electrode segments", or just "segments".

In the lower right corner of FIG. 7A, identified as "III", en electrode configuration is schematically illustrated that has a round central electrode/array 310b of three electrode segments of a first polarity surrounded by an electrode array 320b of three electrode segments of a second polarity. (These round or oval shapes could be altered, as desired or needed. That is, the round central electrode/array 310b could be an oval-shaped electrode array, and the oval-shaped electrode array 320b could be a round electrode array.) As shown in configuration III of FIG. 7A, the three electrode segments of the electrode array 320b are symmetrically positioned within the array 320b, meaning that they are positioned more or less equidistant from each other. However, a symmetrical positioning of the electrode segments within the array is not necessary to stimulate the body tissue at the desired acupoint(s) with some efficacy.

In the upper right corner of FIG. 7A, identified as "IV", an electrode/array configuration is schematically illustrated that has a central electrode array 310c of a first polarity surrounded by an electrode array 320c of four electrode segments of a second polarity. The four electrode segments of the electrode array 320c are arranged symmetrically in a round or oval-shaped array. The four electrode segments of the electrode array 310c are likewise arranged symmetrically in a round or oval-shaped array. While preferred for many configurations, the use of a symmetrical electrode/array, whether as a central electrode array 310 or as a surrounding electrode/array 320, is not always required.

The electrode configurations I, II, III and IV shown schematically in FIG. 7A are only representative of a few electrode configurations that may be used with the present invention. Further, it is to be noted that the central electrode/array 310 need not have the same number of electrode segments as does the surrounding electrode/array 320. Typically, the central electrode/array 310 of a first polarity will be a single electrode; whereas the surrounding electrode/array 320 of a second polarity may have n individual electrode segments, where n is an integer that can vary from 1, 2, 3, . . . n. Thus, for a circumferential electrode array where n=4, there are four electrode segments of the same polarity arranged in circumferential pattern around a central electrode/array. If the circumferential electrode array with n=4 is a symmetrical electrode array, then the four electrode segments will be spaced apart equally in a circumferential pattern around a central electrode/array. When n=1, the circumferential electrode array reduces to a single circumferential segment or a single annular electrode that surrounds a central electrode/array.

Additionally, the polarities of the electrode/arrays may be selected as needed. That is, while the central electrode/array 310 is typically a cathode (−), and the surrounding electrode/array 320 is typically an anode (+), these polarities may be reversed.

As has already been mentioned, the shape of the circumferential electrode/array, whether circular, oval, or other shape, need not necessarily be the same shape as the IEAD housing, unless the circumferential electrode/array is attached to a perimeter edge of the IEAD housing. The IEAD housing may be round, or it may be oval, or it may have a polygon shape, or other shape, as needed to suit the needs of a particular manufacturer and/or patient.

Additional electrode configurations, both symmetrical electrode configurations and non-symmetrical electrode configurations, that may be used with an EA stimulation device as described herein, are illustrated in Appendix A and Appendix B.

Electrical Design

Next, with reference to FIGS. 8A-14, the electrical design and operation of the circuits employed within the IEAD 100 will be described. In particular, a description of the circuits that are used within the IEAD 100 will be described, which circuits allow a thin, high impedance, coin-cell type battery to be employed within the IEAD to provide its operating power over a long period of time. More details associated with the design of the electrical circuits described herein may be found in the following previously-filed U.S. Patent Applications, which applications are incorporated herein by reference: (1) application Ser. No. 13/598,582, filed Aug. 29, 2012, entitled Implantable Electroacupuncture System and Method for Reducing Hypertension; (2) Appl. No. 61/609,875, filed Mar. 12, 2012, entitled Boost Converter Output Control For Implantable Electroacupuncture Device; (3) Appl. No. 61/672,257, filed Jul. 16, 2012, entitled Boost Converter Circuit Surge Control For Implantable Electroacupuncture Device Using Digital Pulsed Shutdown; (4) Appl. No. 61/672,661, filed Jul. 17, 2012, entitled Smooth Ramp-Up Stimulus Amplitude Control For Implantable Electroacupuncture Device; and (5) Appl. No. 61/674,691, filed Jul. 23, 2012, entitled Pulse Charge Delivery Control In An Implantable Electroacupuncture Device.

Figure 8A:
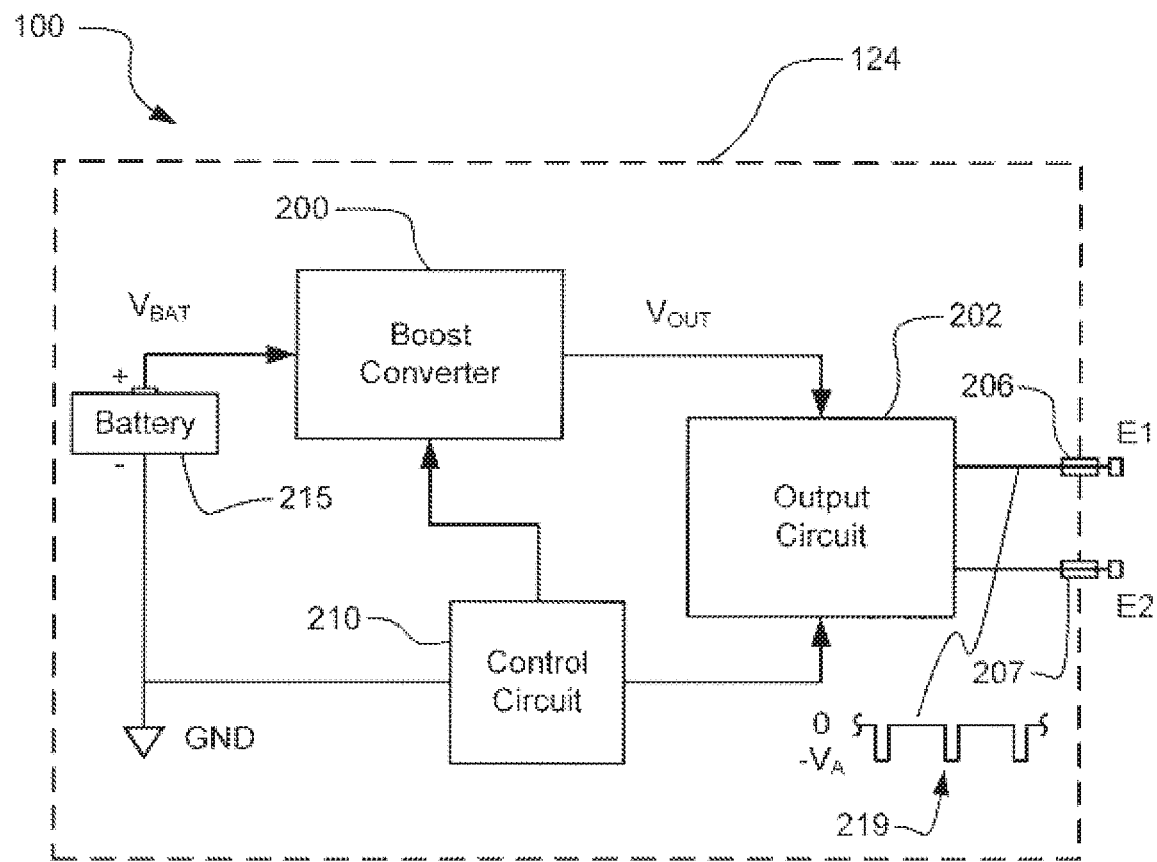
FIG. 8A illustrates a functional block diagram of the electronic circuits used within an IEAD of the type described herein.

FIG. 8A shows a functional block diagram of an implantable electroacupuncture device (IEAD) 100 made in accordance with the teachings disclosed herein. As seen in FIG.

8A, the IEAD 100 uses an implantable battery 215 having a battery voltage $V_{BAT}$. In one preferred embodiment, this battery 215 comprises a lithium battery having a nominal output voltage of 3 V, such as the CR1612 battery manufactured by Panasonic. Also included within the IEAD 100 is a Boost Converter circuit 200, an Output Circuit 202 and a Control Circuit 210. The battery 115, boost converter circuit 200, output circuit 202 and control circuit 210 are all housed within an hermetically sealed housing 124.

As controlled by the control circuit 210, the output circuit 202 of the IEAD 100 generates a sequence of stimulation pulses that are delivered to electrodes E1 and E2, through feed-through terminals 206 and 207, respectively, in accordance with a prescribed stimulation regimen. A coupling capacitor $C_C$ is also employed in series with at least one of the feed-through terminals 206 or 207 to prevent DC (direct current) current from flowing into the patient's body tissue.

Figure 15A:
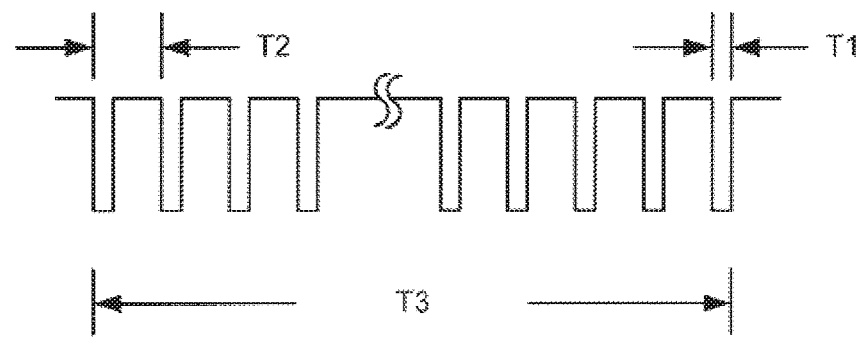
FIG. 15A shows a timing waveform diagram of representative EA stimulation pulses generated by the IEAD device during a stimulation session.

As explained more fully below in connection with the description of FIGS. 15A and 15B, the prescribed stimulation regimen typically comprises a continuous stream of stimulation pulses having a fixed amplitude, e.g., $V_A$ volts, a fixed pulse width, e.g., 0.5 millisecond, and at a fixed frequency, e.g., 2 Hz, during each stimulation session. The stimulation session, also as part of the stimulation regimen, is generated at a very low duty cycle, e.g., for 30 minutes once each week. Other stimulation regimens may also be used, e.g., using a variable frequency for the stimulus pulse during a stimulation session rather than a fixed frequency. Also, the rate of occurrence of the stimulation session may be varied from as short as, e.g., 1 day, to as long as, e.g., 14 days.

In one preferred embodiment, the electrodes E1 and E2 form an integral part of the housing 124. That is, electrode E2 may comprise a circumferential anode electrode that surrounds a cathode electrode E1. The cathode electrode E1, for the embodiment described here, is electrically connected to the case 124 (thereby making the feed-through terminal 206 unnecessary).

In a second preferred embodiment, particularly well-suited for implantable electrical stimulation devices, the anode electrode E2 is electrically connected to the case 124 (thereby making the feed-through terminal 207 unnecessary). The cathode electrode E1 is electrically connected to the circumferential electrode that surrounds the anode electrode E2. That is, the stimulation pulses delivered to the target tissue location (i.e., to the selected acupoint) through the electrodes E1 and E2 are, relative to a zero volt ground (GND) reference, negative stimulation pulses, as shown in the waveform diagram near the lower right hand corner of FIG. 8A.

Thus, in the embodiment described in FIG. 8A, it is seen that during a stimulation pulse the electrode E2 functions as an anode, or positive (+) electrode, and the electrode E1 functions as a cathode, or negative (−) electrode.

The battery 115 provides all of the operating power needed by the EA device 100. The battery voltage $V_{BAT}$ is not the optimum voltage needed by the circuits of the EA device, including the output circuitry, in order to efficiently generate stimulation pulses of amplitude, e.g., $-V_A$ volts. The amplitude $V_A$ of the stimulation pulses is typically many times greater than the battery voltage $V_{BAT}$. This means that the battery voltage must be "boosted", or increased, in order for stimulation pulses of amplitude $V_A$ to be generated. Such "boosting" is done using the boost converter circuit 200. That is, it is the function of the Boost Converter circuit 200 to take its input voltage, $V_{BAT}$, and convert it to another voltage, e.g., $V_{OUT}$, which voltage $V_{OUT}$ is needed by the output circuit 202 in order for the IEAD 100 to perform its intended function.

The IEAD 100 shown in FIG. 8A, and packaged as described above in connection with FIGS. 1-7, advantageously provides a tiny self-contained, coin-sized stimulator that may be implanted in a patient at or near a specified acupoint in order to favorably treat a condition or disease of a patient. The coin-sized stimulator advantageously applies electrical stimulation pulses at very low levels and low duty cycles in accordance with specified stimulation regimens through electrodes that form an integral part of the housing of the stimulator. A tiny coin-cell type battery inside of the coin-sized stimulator provides enough energy for the stimulator to carry out its specified stimulation regimen over a period of several years, despite the fact that the battery typically has a relatively high battery impedance, e.g., greater than 5 ohms, and often as high as 150 ohms, or more. Thus, the coin-sized stimulator, once implanted, provides an unobtrusive, needleless, long-lasting, safe, elegant and effective mechanism for treating certain conditions and diseases that have long been treated by acupuncture or electroacupuncture.

Figure 8B:
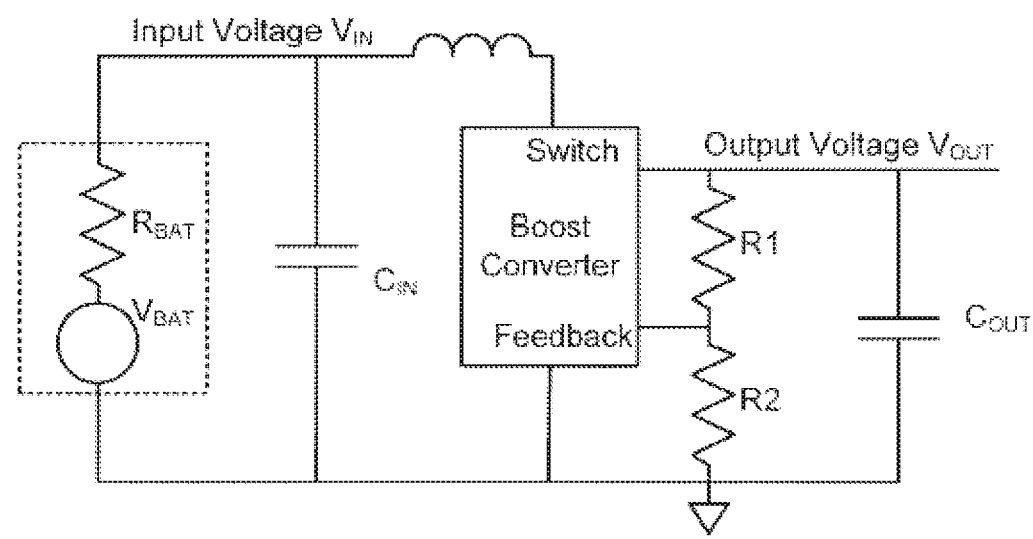
FIG. 8B shows a basic boost converter circuit configuration, and is used to model how the impedance of the battery $R_{BAT}$ can affect its performance.

A boost converter integrated circuit (IC) typically draws current from its power source in a manner that is proportional to the difference between the actual output voltage $V_{OUT}$ and a set point output voltage, or feedback signal. A representative boost converter circuit that operates in this manner is shown in FIG. 8B. At boost converter start up, when the actual output voltage is low compared to the set point output voltage, the current drawn from the power source can be quite large. Unfortunately, when batteries are used as power sources, they have internal voltage losses (caused by the battery's internal impedance) that are proportional to the current drawn from them. This can result in under voltage conditions when there is a large current demand from the boost converter at start up or at high instantaneous output current. Current surges and the associated under voltage conditions can lead to undesired behavior and reduced operating life of an implanted electro-acupuncture device.

In the boost converter circuit example shown in FIG. 8A, the battery is modeled as a voltage source with a simple series resistance. With reference to the circuit shown in FIG. 8A, when the series resistance $R_{BAT}$ is small (5 Ohms or less), the boost converter input voltage $V_{IN}$, output voltage $V_{OUT}$ and current drawn from the battery, $I_{BAT}$, typically look like the waveform shown in FIG. 9A, where the horizontal axis is time, and the vertical axis on the left is voltage, and the vertical axis of the right is current.

Figure 9A:
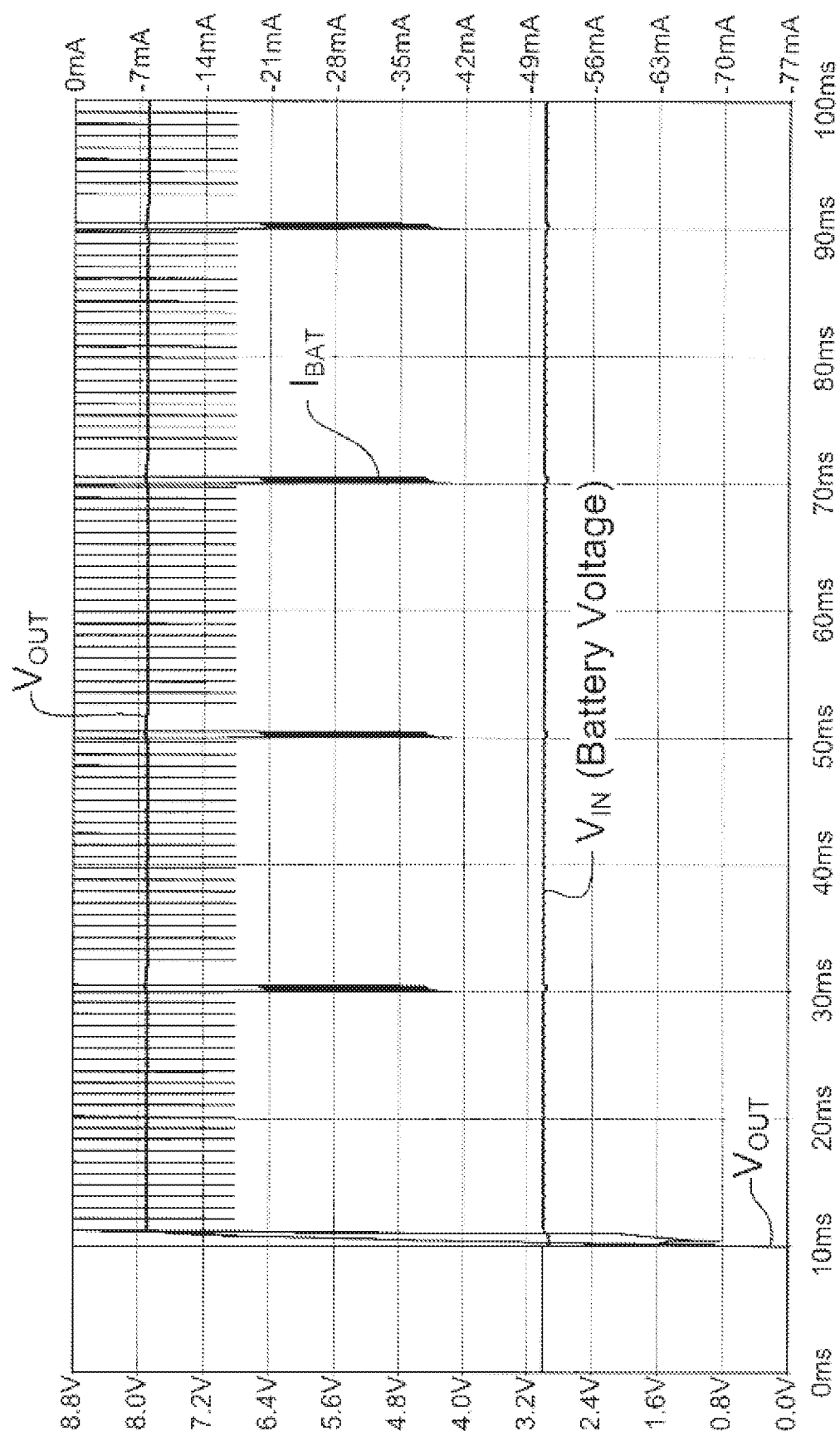
FIG. 9A illustrates a typical voltage and current waveform for the circuit of FIG. 8 when the battery impedance $R_{BAT}$ is small.

Referring to the waveform in FIG. 9A, at boost converter startup (10 ms), there is 70 mA of current drawn from the battery with only ~70 mV of drop in the input voltage $V_{IN}$. Similarly, the instantaneous output current demand for electro-acupuncture pulses draws up to 40 mA from the battery with an input voltage drop of ~40 mV.

Figure 9B:
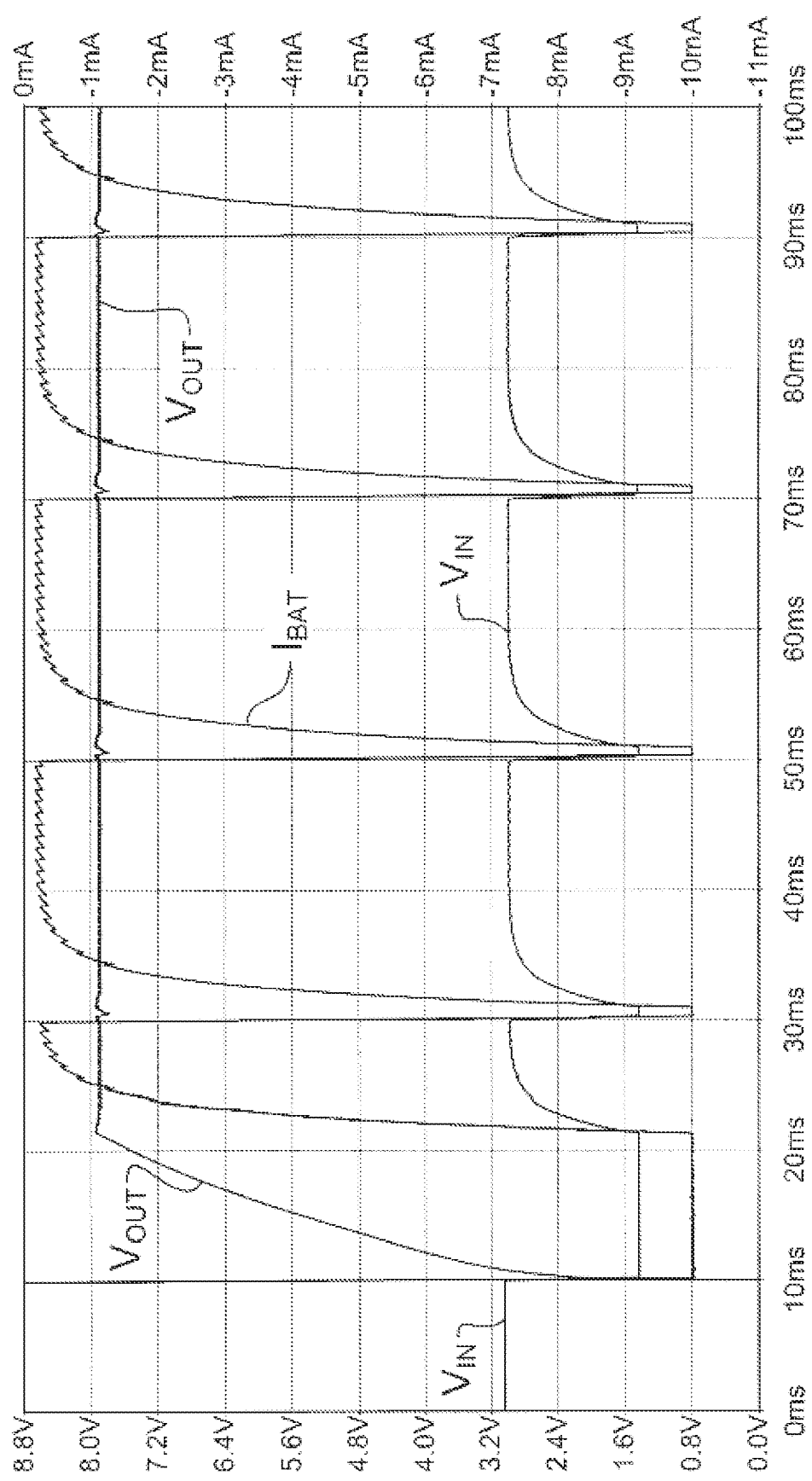
FIG. 9B shows the voltage and current waveform for the circuit of FIG. 8B when the battery impedance $R_{BAT}$ is large.

Disadvantageously, however, a battery with higher internal impedance (e.g., 160 Ohms), cannot source more than a milliampere or so of current without a significant drop in output voltage. This problem is depicted in the timing waveform diagram shown in FIG. 9B. In FIG. 9B, as in FIG. 9A, the horizontal axis is time, the left vertical axis is voltage, and the right vertical axis is current.

As seen in FIG. 9B, as a result of the higher internal battery impedance, the voltage at the battery terminal ($V_{IN}$) is pulled down from 2.9 V to the minimum input voltage of the boost converter (~1.5 V) during startup and during the instantaneous output current load associated with electroacupuncture stimulus pulses. The resulting drops in output voltage $V_{OUT}$ are not acceptable in any type of circuit except an uncontrolled oscillator circuit.

Also, it should be noted that although the battery used in the boost converter circuit is modeled in FIG. 8B as a simple series resistor, battery impedance can arise from the internal design, battery electrode surface area and different types of electrochemical reactions. All of these contributors to battery impedance can cause the voltage of the battery at the battery terminals to decrease as the current drawn from the battery increases.

In a suitably small and thin implantable electroacupuncture device (IEAD) of the type disclosed herein, it is desired to use a higher impedance battery in order to assure a small and thin device, keep costs low, and/or to have low self-discharge rates. The battery internal impedance also typically increases as the battery discharges. This can limit the service life of the device even if a new battery has acceptably low internal impedance. Thus, it is seen that for the IEAD 100 disclosed herein to reliably perform its intended function over a long period of time, a circuit design is needed for the boost converter circuit that can manage the instantaneous current drawn from $V_{IN}$ of the battery. Such current management is needed to prevent the battery's internal impedance from causing $V_{IN}$ to drop to unacceptably low levels as the boost converter circuit pumps up the output voltage $V_{OUT}$ and when there is high instantaneous output current demand, as occurs when stimulation pulses are generated.

Figure 10:
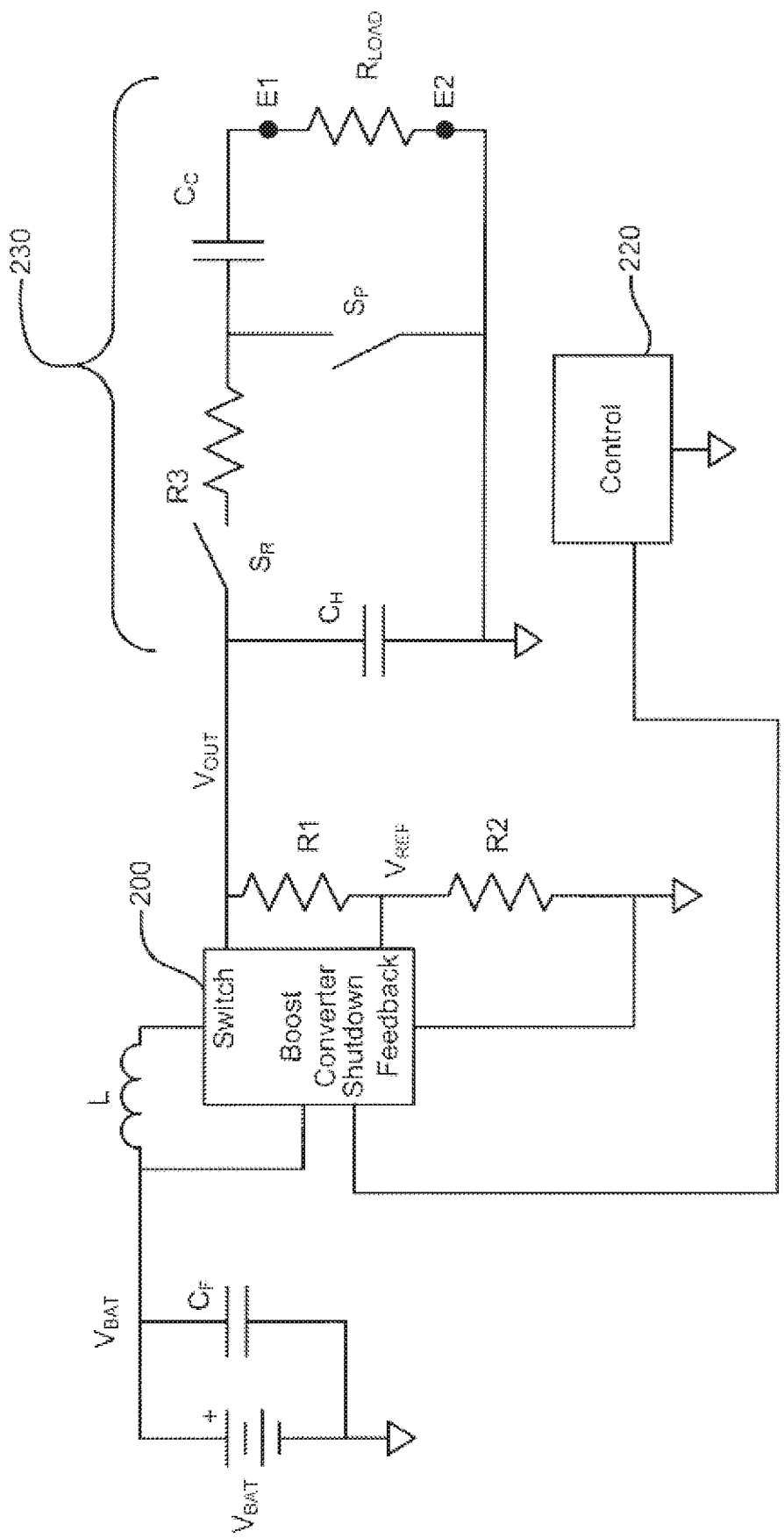
FIG. 10 shows one preferred boost converter circuit and a functional pulse generation circuit configuration for use within the IEAD.

To provide this needed current management, the IEAD 100 disclosed herein employs electronic circuitry as shown in FIG. 10, or equivalents thereof. Similar to what is shown in FIG. 8B, the circuitry of FIG. 10 includes a battery, a boost converter circuit 200, an output circuit 230, and a control circuit 220. The control circuit 220 generates a digital control signal that is used to duty cycle the boost converter circuit 200 ON and OFF in order to limit the instantaneous current drawn from the battery. That is, the digital control signal pulses the boost converter ON for a short time, but then shuts the boost converter down before a significant current can be drawn from the battery. In conjunction with such pulsing, an input capacitance $C_F$ is used to reduce the ripple in the input voltage $V_{IN}$. The capacitor $C_F$ supplies the high instantaneous current for the short time that the boost converter is ON and then recharges more slowly from the battery during the interval that the boost converter is OFF.

A variation of the above-described use of a digital control signal to duty cycle the boost converter circuit 200 ON and OFF is to let the digital control be generated within the boost converter 200 itself (without having to use a separate control circuit 220). In accordance with this variation, the boost converter circuit 200 shuts itself down whenever the battery voltage falls below a predetermined level above that required by the remaining circuitry. For example, the MAX8570 boost converter IC, commercially available from Maxim, shuts down when the applied voltage falls below 2.5 V. This is still a high enough voltage to ensure the microprocessor and other circuitry remain operational. Thus, as soon as the input voltage drops below 2.5 volts, the boost converter circuit shuts down, thereby limiting the instantaneous current drawn from the battery. When the boost converter shuts down, the instantaneous battery current drawn from the battery is immediately reduced a significant amount, thereby causing the input voltage to increase. The boost converter remains shut down until the microprocessor (e.g., the circuit U2 shown in FIG. 13A, described below), and/or other circuitry used with the boost converter, determine that it is time to turn the boost converter back ON. Once turned ON, the boost converter remains ON until, again, the input voltage drops to below 2.5 volts. This pattern continues, with the boost converter being ON for a short time, and OFF for a much longer time, thereby controlling and limiting the amount of current that can be drawn from the battery.

In the circuitry shown in FIG. 10, it is noted that the output voltage $V_{OUT}$ generated by the boost converter circuit 200 is set by the reference voltage $V_{REF}$ applied to the set point or feedback terminal of the boost converter circuit 200. For the configuration shown in FIG. 10, $V_{REF}$ is proportional to the output voltage $V_{OUT}$, as determined by the resistor dividing network of R1 and R2.

The switches $S_P$ and $S_R$, shown in FIG. 10 as part of the output circuit 230, are also controlled by the control circuit 220. These switches are selectively closed and opened to form the EA stimulation pulses applied to the load, $R_{LOAD}$. Before a stimulus pulse occurs, switch $S_R$ is closed sufficiently long for the circuit side of coupling capacitor $C_C$ to be charged to the output voltage, $V_{OUT}$. The tissue side of $C_C$ is maintained at 0 volts by the cathode electrode E2, which is maintained at ground reference. Then, for most of the time between stimulation pulses, both switches $S_R$ and $S_P$ are kept open, with a voltage approximately equal to the output voltage $V_{OUT}$ appearing across the coupling capacitor $C_C$.

At the leading edge of a stimulus pulse, the switch $S_P$ is closed, which immediately causes a negative voltage $-V_{OUT}$ to appear across the load, $R_{LOAD}$, causing the voltage at the anode E1 to also drop to approximately $-V_{OUT}$, thereby creating the leading edge of the stimulus pulse. This voltage starts to decay back to 0 volts as controlled by an RC (resistor-capacitance) time constant that is long compared with the desired pulse width. At the trailing edge of the pulse, before the voltage at the anode E1 has decayed very much, the switch $S_P$ is open and the switch $S_R$ is closed. This action causes the voltage at the anode E1 to immediately (relatively speaking) return to 0 volts, thereby defining the trailing edge of the pulse. With the switch $S_R$ closed, the charge on the circuit side of the coupling capacitor $C_C$ is allowed to charge back to $V_{OUT}$ within a time period controlled by a time constant set by the values of capacitor $C_C$ and resistor R3. When the circuit side of the coupling capacitor $C_C$ has been charged back to $V_{OUT}$, then switch $S_R$ is opened, and both switches $S_R$ and $S_P$ remain open until the next stimulus pulse is to be generated. Then the process repeats each time a stimulus pulse is to be applied across the load.

Thus, it is seen that in one embodiment of the electronic circuitry used within the IEAD 100, as shown in FIG. 10, a boost converter circuit 200 is employed which can be shut down with a control signal. The control signal is ideally a digital control signal generated by a control circuit 220 (which may be realized using a microprocessor or equivalent circuit). The control signal is applied to the low side (ground side) of the boost converter circuit 200 (identified as the "shutdown" terminal in FIG. 10). A capacitor $C_F$ supplies instantaneous current for the short ON time that the control signal enables the boost converter circuit to operate. And, the capacitor CF is recharged from the battery during the relatively long OFF time when the control signal disables the boost converter circuit.

It is also seen that in a variation of the embodiment shown in FIG. 10, a boost converter circuit 200 is used that shuts itself down whenever the input voltage falls below a prescribed threshold, e.g., 2.5 V. The boost converter remains shut down until other circuitry used with the boost converter determines that it is time to turn the boost converter back ON, e.g., whenever the feedback signal indicates the output voltage $V_{OUT}$ has fallen below a prescribed threshold, and/or whenever a prescribed period of time has elapsed since the last stimulus pulse was generated.

Figure 11:
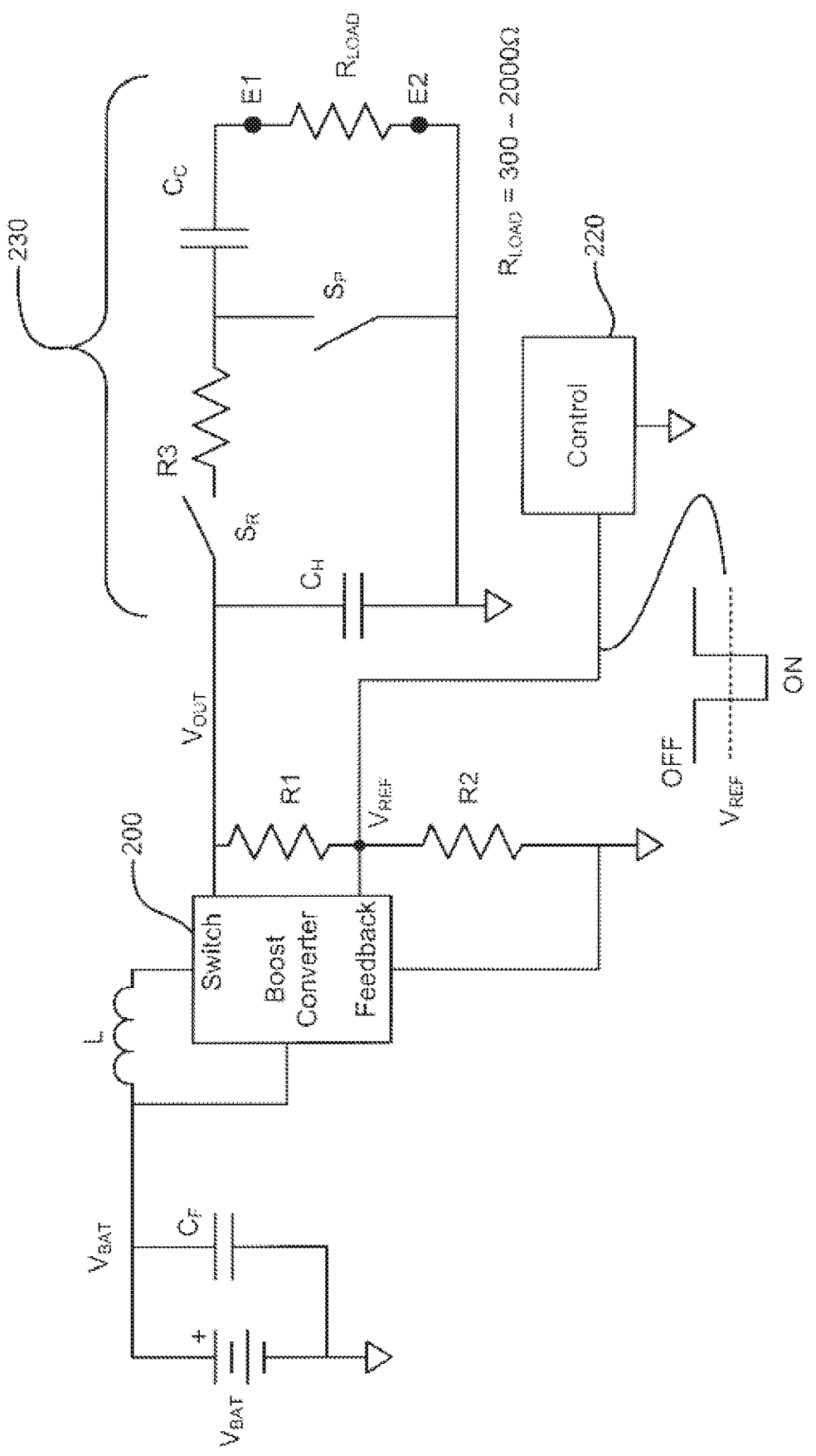
FIG. 11 shows an alternate boost converter circuit configuration and a functional pulse generation circuit for use within the IEAD.

An alternate embodiment of the electronic circuitry that may be used within the IEAD 100 is shown in FIG. 11. This circuit is in most respects the same as the circuitry shown in FIG. 10. However, in this alternate embodiment shown in FIG. 11, the boost converter circuit 200 does not have a specific shut down input control. Rather, as seen in FIG. 11, the boost converter circuit is shut down by applying a control voltage to the feedback input of the boost converter circuit 200 that is higher than $V_{REF}$. When this happens, i.e., when the control voltage applied to the feedback input is greater than $V_{REF}$, the boost converter will stop switching and draws little or no current from the battery. The value of $V_{REF}$ is typically a low enough voltage, such as a 1.2 V band-gap voltage, that a low level digital control signal can be used to disable the boost converter circuit. To enable the boost converter circuit, the control signal can be set to go to a high impedance, which effectively returns the node at the $V_{REF}$ terminal to the voltage set by the resistor divider network formed from R1 and R2. Alternatively the control signal can be set to go to a voltage less than $V_{REF}$.

A low level digital control signal that performs this function of enabling (turning ON) or disabling (turning OFF) the boost converter circuit is depicted in FIG. 11 as being generated at the output of a control circuit 220. The signal line on which this control signal is present connects the output of the control circuit 220 with the $V_{REF}$ node connected to the feedback input of the boost converter circuit. This control signal, as suggested by the waveform shown in FIG. 11, varies from a voltage greater than $V_{REF}$, thereby disabling or turning OFF the boost converter circuit, to a voltage less than $V_{REF}$, thereby enabling or turning the boost converter circuit ON.

Figure 12:
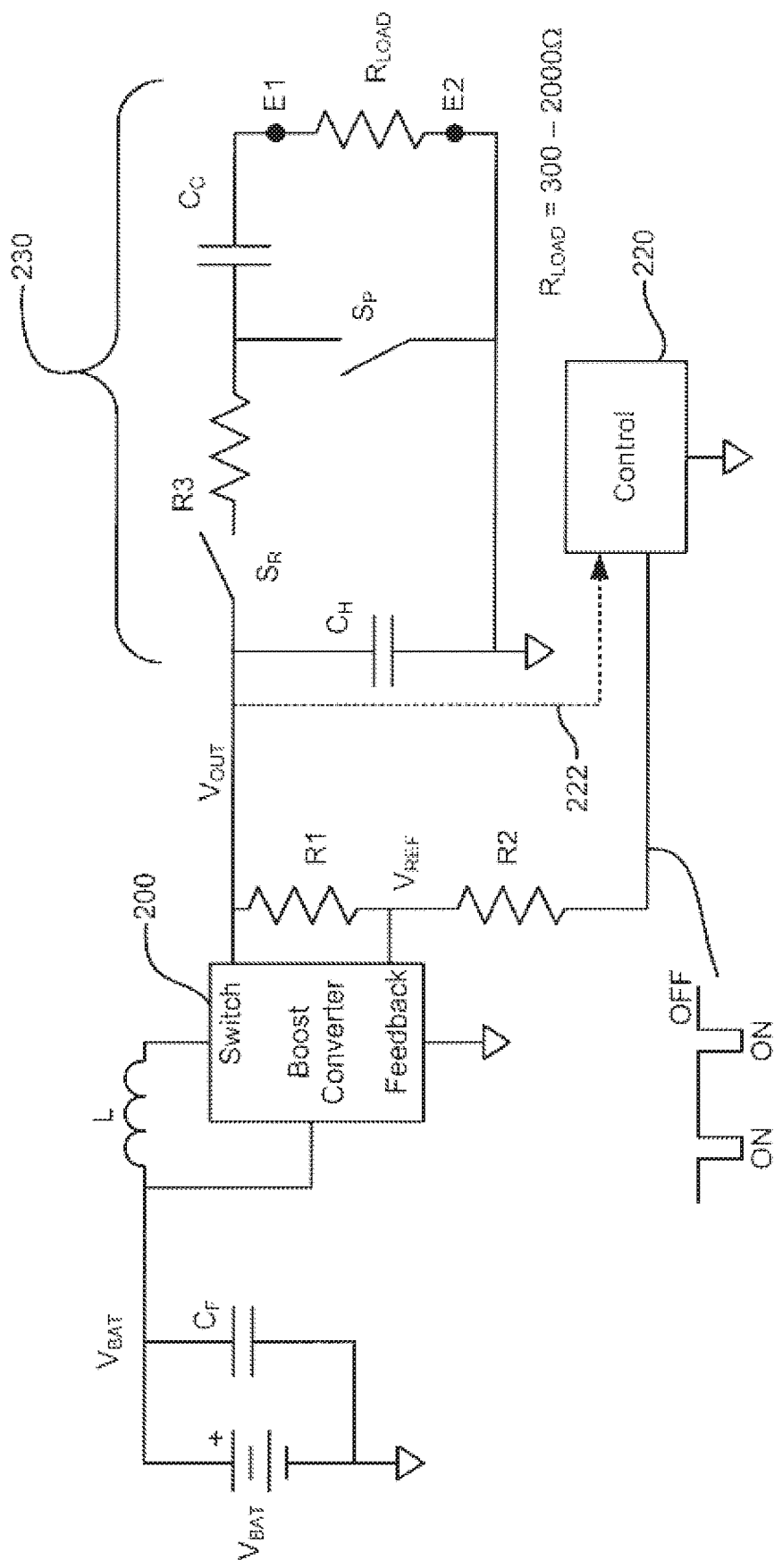
FIG. 12 shows a refinement of the circuit configuration of FIG. 11.

A refinement to the alternate embodiment shown in FIG. 11 is to use the control signal to drive the low side of R2 as shown in FIG. 12. That is, as shown in FIG. 12, the boost converter circuit 200 is shut down when the control signal is greater than $V_{REF}$ and runs when the control signal is less than $V_{REF}$. A digital control signal can be used to perform this function by switching between ground and a voltage greater than $V_{REF}$. This has the additional possibility of delta-sigma modulation control of $V_{OUT}$ if a measurement of the actual $V_{OUT}$ is available for feedback, e.g., using a signal line 222, to the controller.

Figure 13A:
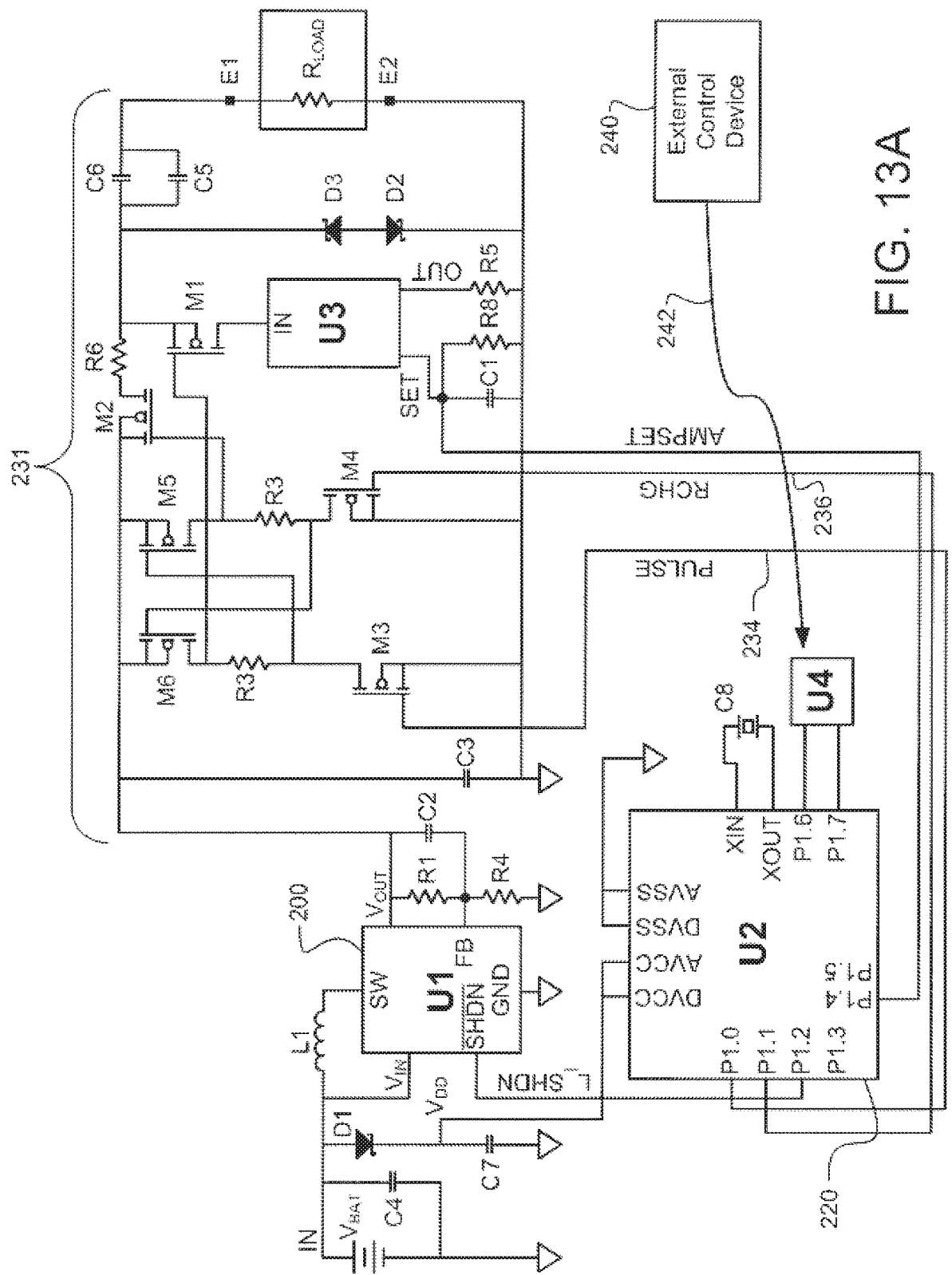
FIG. 13A shows one preferred schematic configuration for an implantable electroacupuncture device (IEAD) that utilizes the boost converter configuration shown in FIG. 10.

One preferred embodiment of the circuitry used in an implantable electroacupuncture device (IEAD) 100 that employs a digital control signal as taught herein is shown in the schematic diagram shown in FIG. 13A. In FIG. 13A, there are basically four integrated circuits (ICs) used as the main components. The IC U1 is a boost converter circuit, and performs the function of the boost converter circuit 200 described previously in connection with FIGS. 8B, 10, 11 and 12.

The IC U2 is a micro-controller IC and is used to perform the function of the control circuit 220 described previously in connection with FIGS. 10, 11 and 12. A preferred IC for this purpose is a MSP430G2452I micro-controller chip made by Texas Instruments. This chip includes 8 KB of Flash memory. Having some memory included with the micro-controller is important because it allows the parameters associated with a selected stimulation regimen to be defined and stored. One of the advantages of the IEAD described herein is that it provides a stimulation regimen that can be defined with just 5 parameters, as taught below in connection with FIGS. 15A and 15B. This allows the programming features of the micro-controller to be carried out in a simple and straightforward manner.

The micro-controller U2 primarily performs the function of generating the digital signal that shuts down the boost converter to prevent too much instantaneous current from being drawn from the battery $V_{BAT}$. The micro-controller U2 also controls the generation of the stimulus pulses at the desired pulse width and frequency. It further keeps track of the time periods associated with a stimulation session, i.e., when a stimulation session begins and when it ends.

The micro-controller U2 also controls the amplitude of the stimulus pulse. This is done by adjusting the value of a current generated by a Programmable Current Source U3. In one embodiment, U3 is realized with a voltage controlled current source IC. In such a voltage controlled current source, the programmed current is set by a programmed voltage appearing across a fixed resistor R5, i.e., the voltage appearing at the "OUT" terminal of U3. This programmed voltage, in turn, is set by the voltage applied to the "SET" terminal of U3. That is, the programmed current source U3 sets the voltage at the "OUT" terminal to be equal to the voltage applied to the "SET" terminal. The programmed current that flows through the resistor R5 is then set by Ohms Law to be the voltage at the "set" terminal divided by R5. As the voltage at the "set" terminal changes, the current flowing through resistor R5 at the "OUT" terminal changes, and this current is essentially the same as the current pulled through the closed switch M1, which is essentially the same current flowing through the load $R_{LOAD}$. Hence, whatever current flows through resistor R5, as set by the voltage across resistor R5, is essentially the same current that flows through the load $R_{LOAD}$. Thus, as the micro-controller U2 sets the voltage at the "set" terminal of U3, on the signal line labeled "AMPSET", it controls what current flows through the load $R_{LOAD}$. In no event can the amplitude of the voltage pulse developed across the load $R_{LOAD}$ exceed the voltage $V_{OUT}$ developed by the boost converter less the voltage drops across the switches and current source.

The switches $S_R$ and $S_P$ described previously in connection with FIGS. 10, 11 and 12 are realized with transistor switches M1, M2, M3, M4, M5 and M6, each of which is controlled directly or indirectly by control signals generated by the micro-controller circuit U2. For the embodiment shown in FIG. 13A, these switches are controlled by two signals, one appearing on signal line 234, labeled PULSE, and the other appearing on signal line 236, labeled RCHG (which is an abbreviation for "recharge"). For the circuit configuration shown in FIG. 13A, the RCHG signal on signal line 236 is always the inverse of the PULSE signal appearing on signal line 234. This type of control does not allow both switch M1 and switch M2 to be open or closed at the same time. Rather, switch M1 is closed when switch M2 is open, and switch M2 is closed, when switch M1 is open. When switch M1 is closed, and switch M2 is open, the stimulus pulse appears across the load, $R_{LOAD}$, with the current flowing through the load, $R_{LOAD}$, being essentially equal to the current flowing through resistor R5. When the switch M1 is open, and switch M2 is closed, no stimulus pulse appears across the load, and the coupling capacitors C5 and C6 are recharged through the closed switch M2 and resistor R6 to the voltage $V_{OUT}$ in anticipation of the next stimulus pulse.

The circuitry shown in FIG. 13A is only exemplary of one type of circuit that may be used to control the pulse width, amplitude, frequency, and duty cycle of stimulation pulses applied to the load, $R_{LOAD}$. Any type of circuit, or control, that allows stimulation pulses of a desired magnitude (measured in terms of pulse width, frequency and amplitude, where the amplitude may be measured in current or voltage) to be applied through the electrodes to the patient at the specified acupoint at a desired duty cycle (stimulation session duration and frequency) may be used. However, for the circuitry to perform its intended function over a long period of time, e.g., years, using only a small energy source, e.g., a small coin-sized battery having a high battery impedance and a relatively low capacity, the circuitry must be properly managed and controlled to prevent excessive current draw from the battery.

It is also important that the circuitry used in the IEAD 100, e.g., the circuitry shown in FIG. 10, 11, 12, 13A, or equivalents thereof, have some means for controlling the stimulation current that flows through the load, $R_{LOAD}$, which load may be characterized as the patient's tissue impedance at and around the acupoint or other target location that is being stimulated. This tissue impedance, as shown in FIGS. 11 and 12, may typically vary from between about 300 ohms to 2000 ohms. Moreover, it not only varies from one patient to another, but it varies over time. Hence, there is a need to control the current that flows through this variable load, $R_{LOAD}$. One way of accomplishing this goal is to control the stimulation current, as opposed to the stimulation voltage, so that the same current will flow through the tissue load regardless of changes that may occur in the tissue impedance over time. The use of a voltage controlled current source U3, as shown in FIG. 13A, is one way to satisfy this need.

Still referring to FIG. 13A, a fourth IC U4 is connected to the micro-controller U2. For the embodiment shown in FIG. 13A, the IC U4 is an electromagnetic field sensor, and it allows the presence of an externally-generated (non-implanted) electromagnetic field to be sensed. An "electromagnetic" field, for purposes of this application includes magnetic fields, radio frequency (RF) fields, light fields, and the like. The electromagnetic sensor may take many forms, such as any wireless sensing element, e.g., a pickup coil or RF detector, a photon detector, a magnetic field detector, and the like. When a magnetic sensor is employed as the electromagnetic sensor U4, the magnetic field is generated using an External Control Device (ECD) 240 that communicates wirelessly, e.g., through the presence or absence of a magnetic field, with the magnetic sensor U4. (A magnetic field, or other type of field if a magnetic field is not used, is symbolically illustrated in FIG. 13A by the wavy line 242.) In its simplest form, the ECD 240 may simply be a magnet, and modulation of the magnetic field is achieved simply by placing or removing the magnet next to or away from the IEAD. When other types of sensors (non-magnetic) are employed, the ECD 240 generates the appropriate signal or field to be sensed by the sensor that is used.

Use of the ECD 240 provides a way for the patient, or medical personnel, to control the IEAD 100 after it has been implanted (or before it is implanted) with some simple commands, e.g., turn the IEAD ON, turn the IEAD OFF, increase the amplitude of the stimulation pulses by one increment, decrease the amplitude of the stimulation pulses by one increment, and the like. A simple coding scheme may be used to differentiate one command from another. For example, one coding scheme is time-based. That is, a first command is communicated by holding a magnet near the IEAD 100, and hence near the magnetic sensor U4 contained within the IEAD 100, for differing lengths of time. If, for example, a magnet is held over the IEAD for at least 2 seconds, but no more than 7 seconds, a first command is communicated. If a magnet is held over the IEAD for at least 11 seconds, but no more than 18 seconds, a second command is communicated, and so forth.

Another coding scheme that could be used is a sequence-based coding scheme. That is, application of 3 magnetic pulses may be used to signal one external command, if the sequence is repeated 3 times. A sequence of 2 magnetic pulses, repeated twice, may be used to signal another external command. A sequence of one magnetic pulse, followed by a sequence of two magnetic pulses, followed by a sequence of three magnetic pulses, may be used to signal yet another external command.

Other simple coding schemes may also be used, such as the letters AA, RR, HO, BT, KS using international Morse code. That is, the Morse code symbols for the letter "A" are dot dash, where a dot is a short magnetic pulse, and a dash is a long magnetic pulse. Thus, to send the letter A to the IEAD 100 using an external magnet, the user would hold the magnet over the area where the IEAD 100 is implanted for a short period of time, e.g., one second or less, followed by holding the magnet over the IEAD for a long period of time, e.g., more than one second.

More sophisticated magnetic coding schemes may be used to communicate to the micro-controller chip U2 the operating parameters of the IEAD 100. For example, using an electromagnet controlled by a computer, the pulse width, frequency, and amplitude of the EA stimulation pulses used during each stimulation session may be pre-set. Also, the frequency of the stimulation sessions can be pre-set. Additionally, a master reset signal can be sent to the device in order to re-set these parameters to default values. These same operating parameters and commands may be re-sent at any time to the IEAD 100 during its useful lifetime should changes in the parameters be desired or needed.

Figure 13B:
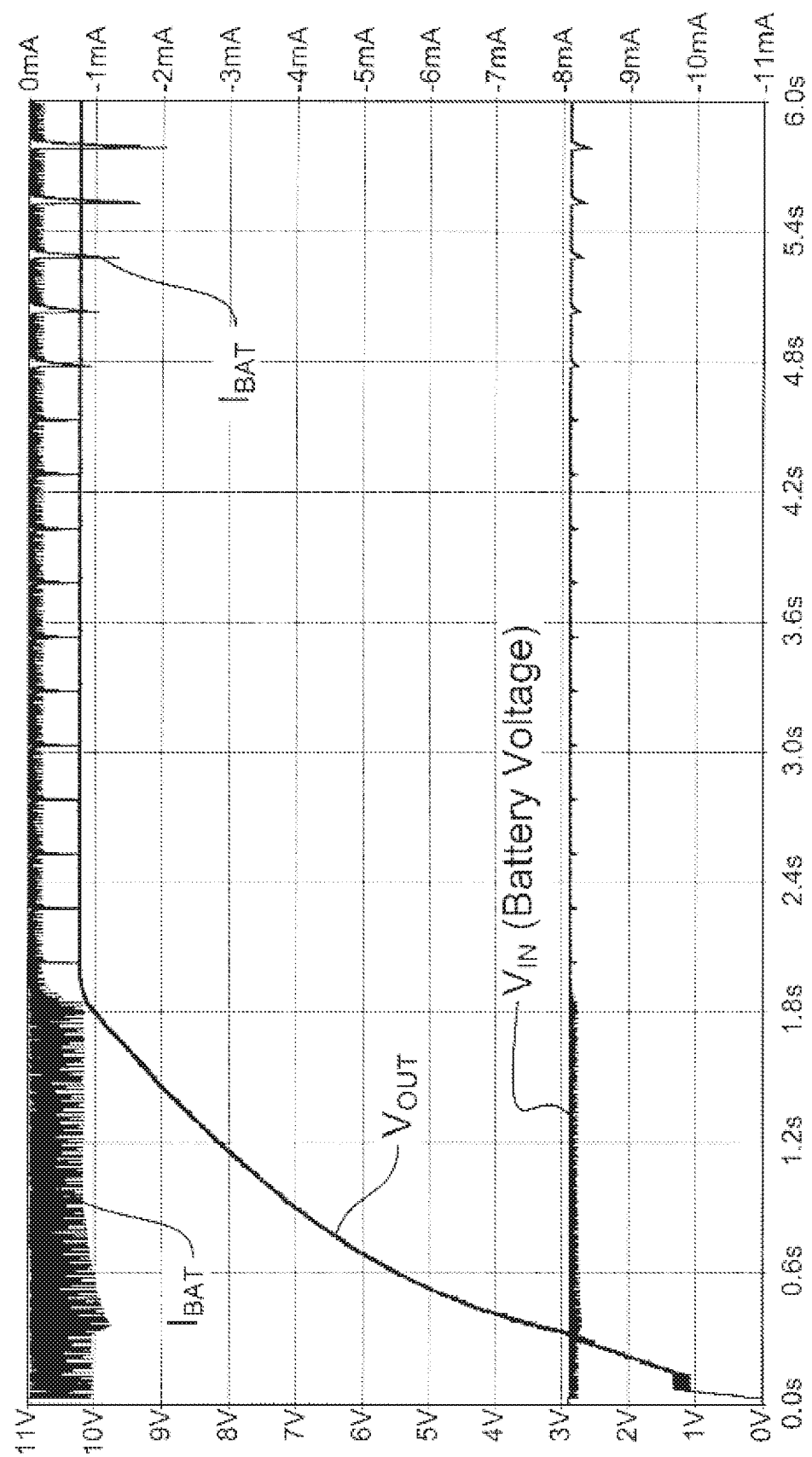
FIG. 13B shows current and voltage waveforms associated with the operation of the circuit shown in FIG. 13A.

The current and voltage waveforms associated with the operation of the IEAD circuitry of FIG. 13A are shown in FIG. 13B. In FIG. 13B, the horizontal axis is time, the left vertical axis is voltage, and the right vertical axis is current. The battery in this example has 160 Ohms of internal impedance.

Referring to FIGS. 13A and 13B, during startup, the boost converter ON time is approximately 30 microseconds applied every 7.8 milliseconds. This is sufficient to ramp the output voltage $V_{OUT}$ up to over 10 V within 2 seconds while drawing no more than about 1 mA from the battery and inducing only 150 mV of input voltage ripple.

The electroacupuncture (EA) simulation pulses resulting from operation of the circuit of FIG. 13A have a width of 0.5 milliseconds and increase in amplitude from approximately 1 mA in the first pulse to approximately 15 mA in the last pulse. The instantaneous current drawn from the battery is less than 2 mA for the EA pulses and the drop in battery voltage is less than approximately 300 mV. The boost converter is enabled (turned ON) only during the instantaneous output current surges associated with the 0.5 milliseconds wide EA pulses.

Figure 14:
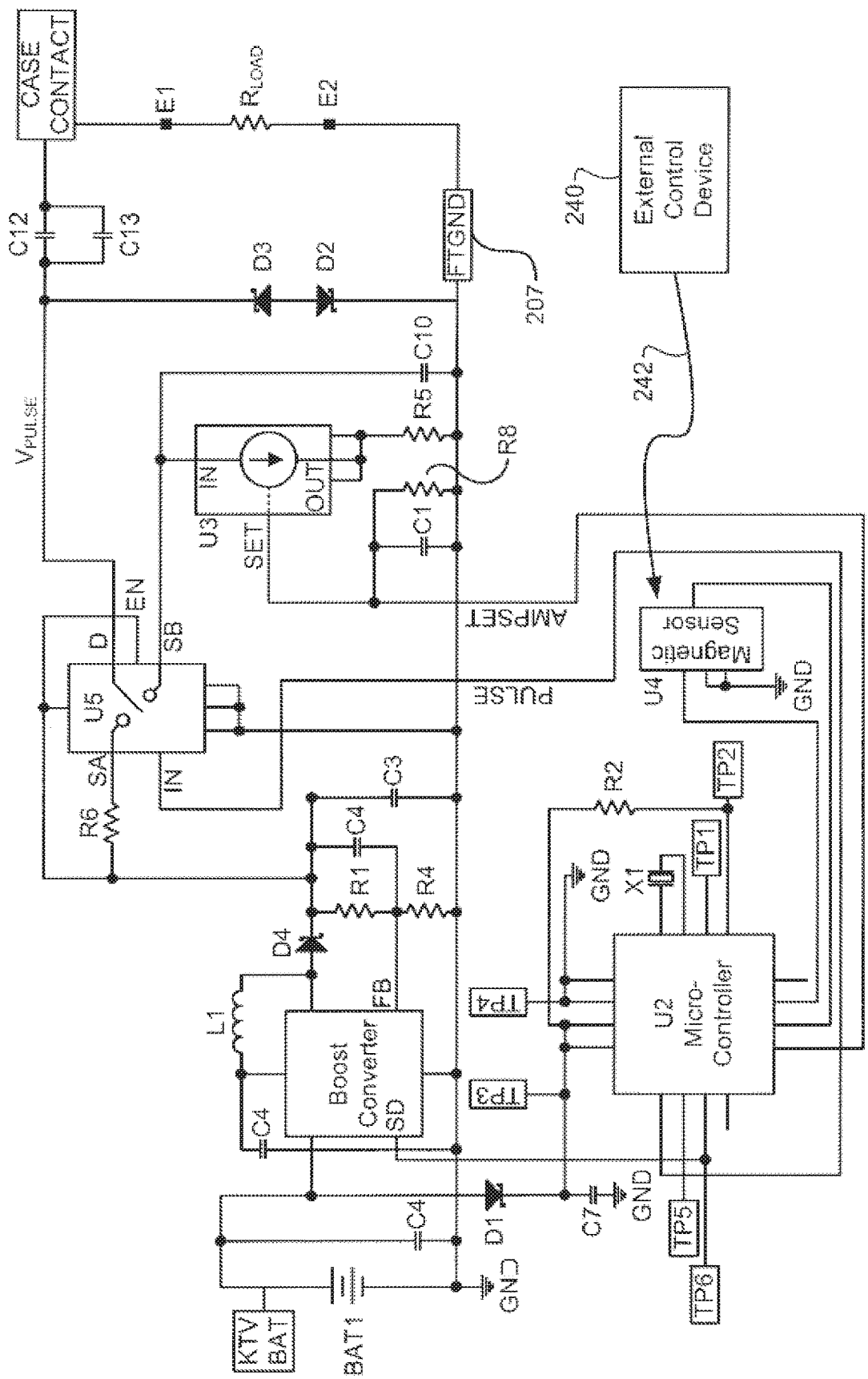
FIG. 14 shows another preferred schematic configuration for an IEAD similar to that shown in FIG. 13A, but which uses an alternate output circuitry configuration for generating the stimulus pulses.

Another preferred embodiment of the circuitry used in an implantable electroacupuncture device (IEAD) 100 that employs a digital control signal as taught herein is shown in the schematic diagram of FIG. 14. The circuit shown in FIG. 14 is, in most respects, very similar to the circuit described previously in connection with FIG. 13A. What is new in FIG. 14 is the inclusion of a Schottky diode D4 at the output terminal LX of the boost convertor U1 and the inclusion of a fifth integrated circuit (IC) U5 that essentially performs the same function as the switches M1-M6 shown in FIG. 13A.

The Schottky diode D4 helps isolate the output voltage $V_{OUT}$ generated by the boost converter circuit U1. This is important in applications where the boost converter circuit U1 is selected and operated to provide an output voltage $V_{OUT}$ that is four or five times as great as the battery voltage, $V_{BAT}$. For example, in the embodiment for which the circuit of FIG. 14 is designed, the output voltage $V_{OUT}$ is designed to be nominally 15 volts using a battery that has a nominal battery voltage of only 3 volts. (In contrast, the embodiment shown in FIG. 13A is designed to provide an output voltage that is nominally 10-12 volts, using a battery having a nominal output voltage of 3 volts.)

The inclusion of the fifth IC U5 in the circuit shown in FIG. 14 is, as indicated, used to perform the function of a switch. The other ICs shown in FIG. 14, U1 (boost converter), U2 (micro-controller), U3 (voltage controlled programmable current source) and U4 (electromagnetic sensor) are basically the same as the IC's U1, U2, U3 and U4 described previously in connection with FIG. 13A.

The IC U5 shown in FIG. 14 functions as a single pole/double throw (SPDT) switch. Numerous commercially-available ICs may be used for this function. For example, an ADG1419 IC, available from Analog Devices Incorporated (ADI) may be used. In such IC U5, the terminal "D" functions as the common terminal of the switch, and the terminals "SA" and "SB" function as the selected output terminal of the switch. The terminals "IN" and "EN" are control terminals to control the position of the switch. Thus, when there is a signal present on the PULSE line, which is connected to the "IN" terminal of U5, the SPDT switch U5 connects the "D" terminal to the "SB" terminal, and the SPDT switch U5 effectively connects the cathode electrode E1 to the programmable current source U3. This connection thus causes the programmed current, set by the control voltage AMPSET applied to the SET terminal of the programmable current source U3, to flow through resistor R5, which in turn causes essentially the same current to flow through the load, $R_{LOAD}$, present between the electrodes E1 and E2. When a signal is not present on the PULSE line, the SPDT switch U5 effectively connects the cathode electrode E1 to the resistor R6, which allows the coupling capacitors C12 and C13 to recharge back to the voltage $V_{OUT}$ provided by the boost converter circuit U2.

Figure 14A:
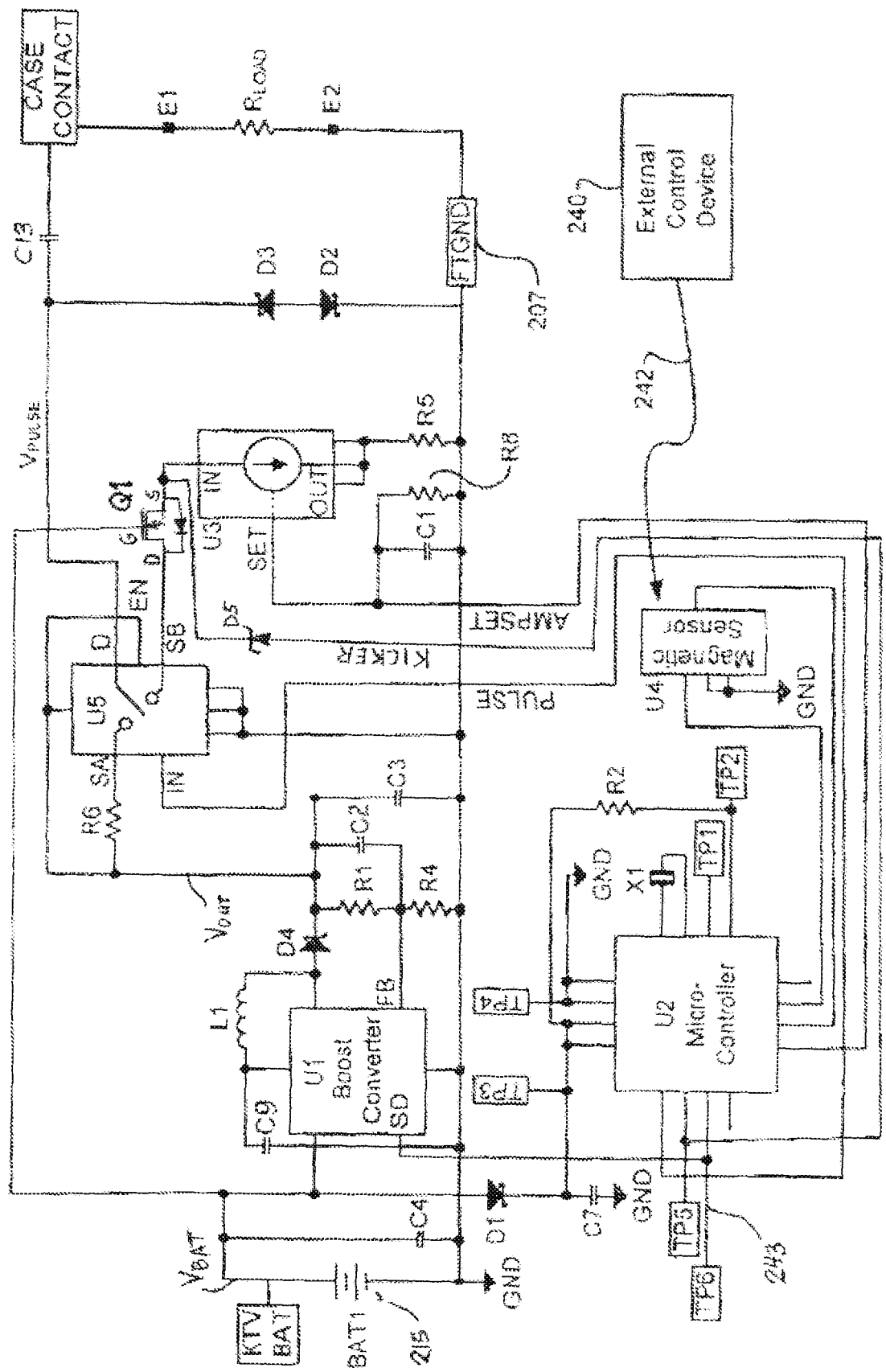
FIG. 14A depicts yet a further preferred schematic configuration for an IEAD similar to that shown in FIG. 13A or FIG. 14, but which includes additional enhancements and circuit features.

Yet another preferred embodiment of the circuitry used in an implantable electroacupuncture device (IEAD) 100 that employs an ON-OFF approach to duty-cycle modulate the boost converter as a tool for limiting the amount of instantaneous battery current drawn from the high impedance battery 215 is shown in the schematic diagram of FIG. 14A. The circuit shown in FIG. 14A is, in most respects, very similar to, or the same as, the circuit described previously in connection with FIG. 14 or FIG. 13A, and that description will not be repeated here. What is new in FIG. 14A are the addition of elements and features that address additional issues associated with the operation of an IEAD 100.

One feature included in the circuitry of FIG. 14A, which is described briefly above in connection with the description of FIG. 10, is that the boost converter circuit U1 is modulated ON and OFF using digital control generated within the boost converter circuit U1 itself. In accordance with this variation, the boost converter circuit 200 shuts itself down whenever the battery voltage falls below a predetermined level above that required by the remaining circuitry. For example, in the embodiment shown in FIG. 14A, the boost converter circuit U1 is realized using a MAX8570 boost converter IC, commercially available from Maxim, or equivalents thereof. This particular boost converter IC shuts down when the applied voltage, $V_{BAT}$, falls below 2.5 V. Advantageously, a battery voltage of 2.5 volts is still a high enough voltage to ensure the microcontroller IC U2, and other circuitry associated with the operation of the IEAD 100, remain operational.

Thus, in operation, as soon as the battery voltage drops below 2.5 volts, the boost converter circuit U1 shuts down, thereby limiting the instantaneous current drawn from the battery. When the boost converter U1 shuts down, the instantaneous battery current drawn from the battery is immediately reduced a significant amount, thereby causing the battery voltage $V_{BAT}$ to increase.

As the battery voltage $V_{BAT}$ increases, the boost converter circuit U1 remains shut down until the microcontroller U2 determines that it is time to turn the boost converter back ON. This turn ON typically occurs in one of two ways: (1) just prior to the delivery of the next stimulus pulse, a turn ON signal may be applied to the Shutdown ("SD") terminal, signal line 243, of the boost converter circuit U1; or (2) as soon as the battery voltage, $V_{BAT}$, has increased a sufficient amount, as sensed at the feedback terminal FB of the boost converter circuit U1, the circuits within the boost converter circuit U1 are automatically turned back ON, allowing the output voltage $V_{OUT}$ to build up to a voltage level needed by the switch circuit U5 and the current source circuit U3 to generate an output stimulus pulse of the desired amplitude when the next PULSE signal is applied to the IN terminal of the switch U5 by the microcontroller U2.

Once turned ON, the boost converter remains ON until, again, the input voltage drops below 2.5 volts. This pattern continues, with the boost converter being ON for a short time, and OFF for a much longer time (typically, the duty cycle associated with this ON/OFF operation of the boost converter circuit U1 is no greater than about 0.01), thereby controlling and limiting the amount of current that is drawn from the battery. This ON/OFF action of U1 assures that the battery voltage, $V_{BAT}$, always remains sufficiently high to permit operation of all the critical circuits of the IEAD 100 (principally the circuits of the microcontroller U2), except the boost converter circuit U1.

In a preferred implementation, the microcontroller circuit U2 used in FIG. 14A comprises an MSP430G2452IRSA 16 microcontroller, commercially available from Texas Instruments, or equivalent microcontroller The current source circuit U3 comprises a LT3092 programmable current source commercially available form Linear Technology, or equivalents thereof. The sensor circuit U4 comprises an AS-M15SA-R magnetic sensor, commercially available from Murata, or equivalents thereof. And, the switch circuit U5 comprises an ADG1419BCPZ single pole double throw analog switch commercially available from Analog Devices, or equivalents thereof.

Another feature or enhancement provided by the circuit implementation depicted in FIG. 14A relates to removing, or at least minimizing, some undesirable leading edge transients that are seen in the output stimulus pulses generated by the circuitry of FIG. 14A. The solution to remove or mitigate the occurrence of such leading edge transients is to insert an N-MOSFET transistor switch Q1 at the input terminal, IN, of the programmable current source circuit U3. This switch Q1 acts as a "cascode" stage that maintains a more constant voltage across the current source U3 as the output current and/or load resistance changes. The gate (G) terminal of the switch Q1 is driven by the battery voltage, $V_{BAT}$, which means the voltage at the source terminal (S) of switch Q1, which is connected to the IN terminal of the current source U3, is limited to roughly $V_{BAT}$-$V_{GS}$, where $V_{GS}$ is the threshold voltage across the gate (G)-source(S) terminals of Q1.

Use of this N-MOSFET switch Q1 as depicted in FIG. 14A advantageously reduces the transient leading edge of the stimulus pulse because the capacitance looking into Q1 is much less than is seen when looking into the current source circuit U3 because of the Miller effect. That is, there is considerable loop gain in the operation of the U3 current source circuit to servo the current. This loop gain directly scales the input capacitance so that there is a much larger leading edge spike on the pulse. This in turn causes a 30 to 40 microsecond transient at the leading edge of the current pulse as the current source U3 recovers current regulation.

Figure 14B:
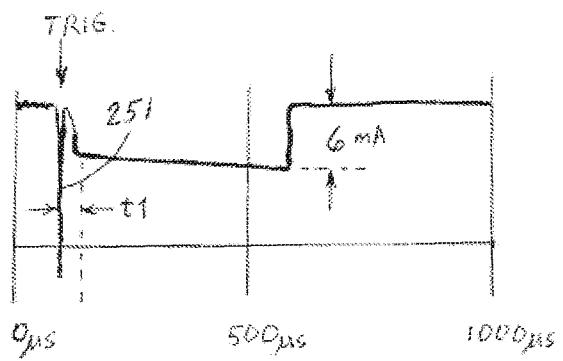
FIGS. 14B and 14C show timing waveform diagrams that illustrate the operation of the circuit of FIG. 14 before (FIG. 14B) and after (FIG. 14C) the addition of a cascode stage to the IEAD circuitry that removes some undesirable transients from the leading edge of the stimulus pulse.

An example of this leading edge transient is illustrated in the timing waveform diagram of FIG. 14B. In FIG. 14B (as well as in FIGS. 14C, 14D and 14E, which all show similar timing waveform diagrams), the horizontal axis is time and the vertical axis is voltage, which (assuming a resistive load of 600 ohms) may readily be converted to current, as has been done in these figures. The stimulus pulse begins at a trigger location near the left edge of the waveform, labeled TRIG. As seen in FIG. 14B, immediately after the trigger point, which should mark the beginning or leading edge of the stimulus pulse, an initial spike 251 occurs that has a magnitude on the order of twice the amplitude of the stimulus pulse. This spike 251 shoots down (as the waveform is oriented in the figures) and then shoots back up, and eventually, after a delay of t1 microseconds, becomes the leading edge of the pulse. The delay t1 is about 30-40 microseconds, which means that the leading edge of the stimulus pulse is delayed 30-40 microseconds. Having a leading edge delay of this magnitude is not a desirable result.

Figure 14C:
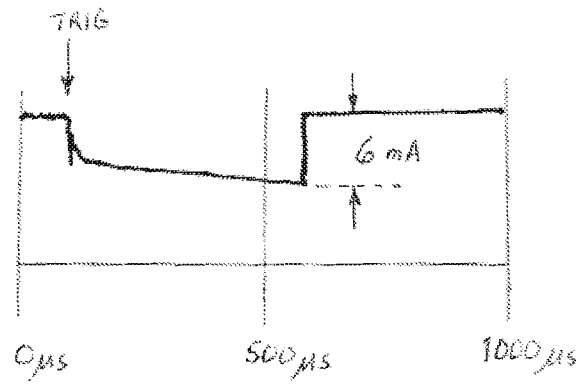

Next, with the cascode stage (comprising the switch Q1) connected to the input terminal, IN, of the current source U3, the stimulus pulse is again illustrated. Because the cascode stage significantly reduces the input capacitance looking into the drain (D) terminal of the switch Q1, the leading edge transient is significantly reduced, as illustrated in the timing waveform diagram of FIG. 14C. As seen in FIG. 14C, the leading edge transient has all but disappeared, and the delay t1 between the trigger point and the leading edge of the stimulus pulse is negligible.

Figure 14D:
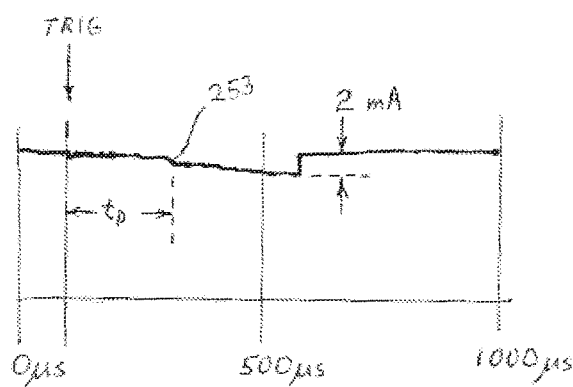
FIGS. 14D and 14E illustrate timing waveform diagrams that show the operation of the circuit of FIG. 14 before (FIG. 14D) and after (FIG. 14E) the addition of circuitry that addresses a delay when starting the current regulator U3 for low amplitude stimulus pulses.

Another feature or enhancement provided by the circuitry of FIG. 14A is to address a delay that is seen when starting up the programmable current source U3 at low pulse amplitudes, (e.g., less than about 3 mA). A typical current stimulus output for the IEAD is on the order of 15-25 mA. When a much smaller amplitude current stimulus is used, e.g., 1.5-3 mA, the control signal that defines this smaller amplitude pulse is significantly less than the one used to define the more typical stimulus amplitudes of 15-25 mA. Such a small control signal lengthens the delay, $t_D$, between the trigger point, TRIG, and the leading edge 253 of the stimulus pulse. FIG. 14D illustrates this long delay, $t_D$, which is on the order of 200 microseconds.

The address the problem illustrated in the waveform diagram of FIG. 14D, a Schottky diode D5 is connected in the circuit of FIG. 14A from an output port on the microcontroller circuit U2 to the input port, IN, of the current source circuit U3. In a preferred implementation of the circuit of FIG. 14A, this Schottky diode D5 is realized using a BAT54XV2DKR diode, commercially available from Fairchild Semiconductor. This diode is used to warm-up or "kick start" the circuit U3 when the pulse amplitude is low so that there is less of a delay, $t_D$, before current is regulated at the start of the pulse. Since the cascode stage Q1 keeps the drop across U3 low, U3 can be driven directly from the microcontroller U2 at the start of the pulse without significantly changing the pulse characteristics (e.g., amplitude or timing) in such a way that the delay, $t_D$, before current is regulated at the start of the pulse can be reduced.

Figure 14E:
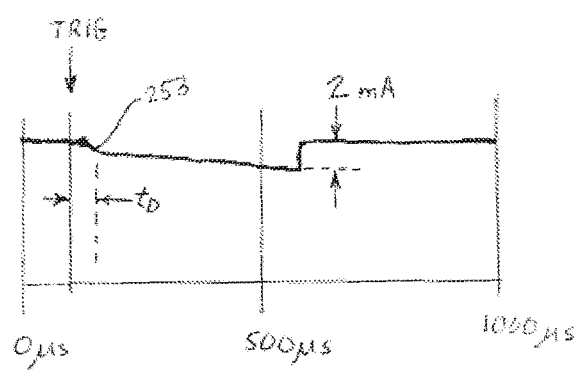

FIG. 14E illustrates the timing waveform diagram achieved using the circuit of FIG. 14A with the diode D5 inserted so as to allow the microcontroller U2 to directly drive, or "kick start", the current source circuit U3 at the start of the pulse. As seen in FIG. 14E, the delay, $t_D$, realized with the "kick start" has been significantly reduced from what it was without the "kick start" (as shown in FIG. 14D), e.g., from about 200 microseconds to about 40 microseconds, or less. Thus, this "kick start" feature shortens the undesired delay, $t_D$, by at least a factor of about 5.

From the above description, it is seen that an implantable IEAD 100 is provided that uses a digital control signal to duty-cycle limit the instantaneous current drawn from the battery by a boost converter. Three different exemplary configurations (FIGS. 10, 11 and 12) are taught for achieving this desired result, and three exemplary circuit designs, or implementations, have been presented that may be used to realize the desired results (FIGS. 13A, 14 and 14A). One configuration (FIG. 12) teaches the additional capability to delta-sigma modulate the boost converter output voltage.

Delta-sigma modulation is well described in the art. Basically, it is a method for encoding analog signals into digital signals or higher-resolution digital signals into lower-resolution digital signals. The conversion is done using error feedback, where the difference between the two signals is measured and used to improve the conversion. The low-resolution signal typically changes more quickly than the high-resolution signal and it can be filtered to recover the high resolution signal with little or no loss of fidelity. Delta-sigma modulation has found increasing use in modern electronic components such as converters, frequency synthesizers, switched-mode power supplies and motor controllers. See, e.g., Wikipedia, Delta-sigma modulation.

Use and Operation

With the implantable electroacupuncture device (IEAD) 100 in hand, the IEAD 100 may be used most effectively to treat a specified disease or medical condition of the patent by first pre-setting stimulation parameters that the device will use during a stimulation session. FIG. 15A shows a timing waveform diagram illustrating the EA stimulation parameters used by the IEAD to generate EA stimulation pulses. As seen in FIG. 15A, there are basically four parameters associated with a stimulation session. The time T1 defines the duration (or pulse width) of a stimulus pulse. The time T2 defines the time between the start of one stimulus pulse and the start of the next stimulus pulse. The time T2 thus defines the period associated with the frequency of the stimulus pulses. The frequency of the stimulation pulses is equal to 1/T2. The ratio of T1/T2 is typically quite low, e.g., less than 0.01. The duration of a stimulation session is dictated or defined by the time period T3. The amplitude of the stimulus pulses is defined by the amplitude A1. This amplitude may be expressed in either voltage or current.

Figure 15B:
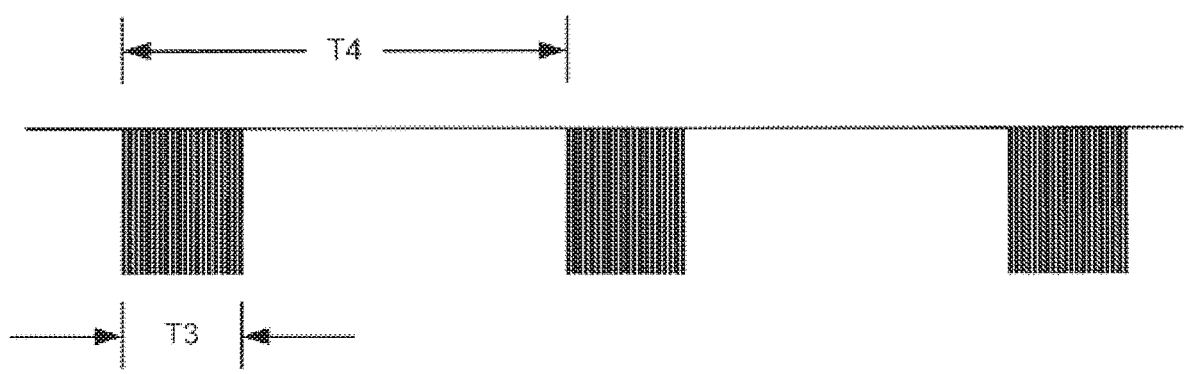
FIG. 15B shows a timing waveform diagram of multiple stimulation sessions, and illustrates the waveforms on a more condensed time scale.

Turning next to FIG. 15B, a timing waveform diagram is shown that illustrates the manner in which the stimulation sessions are administered in accordance with a preferred stimulation regimen. FIG. 15B shows several stimulation sessions of duration T3, and how often the stimulation sessions occur. The stimulation regimen thus includes a time period T4 which sets the time period from the start of one stimulation session to the start of the next stimulation session. T4 thus is the period of the stimulation session frequency, and the stimulation session frequency is equal to 1/T4.

In order to allow the applied stimulation to achieve its desired effect on the body tissue at the selected target stimulation site, the period of the stimulation session T4 may be varied when the stimulation sessions are first applied. This can be achieved by employing a simple algorithm within the circuitry of the EA device that changes the value of T4 in an appropriate manner. For example, at start up, the period T4 may be set to a minimum value, T4 (min). Then, as time goes on, the value of T4 may be gradually increased until a desired value of T4, T4 (final) is reached.

By way of example, if T4 (min) is 1 day, and T4 (final) is 7 days, the value of T4 may vary as follows once the stimulation sessions begin: T4=1 day for the duration between the first and second stimulation sessions, then 2 days for the duration between the second and third stimulation sessions, then 4 days for the duration between the third and fourth stimulation sessions, and then finally 7 days for the duration between all subsequent stimulation sessions after the fourth stimulation session.

Rather than increasing the value of T4 from a minimum value to a maximum value using a simple doubling algorithm, as described in the previous paragraph, an enhancement is to use a table of session durations and intervals whereby the automatic session interval can be shorter for the first week or so. For example the $1^{st}$ 30 minute session could be delivered after 1 day. The $2^{nd}$ 30 minute session could be delivered after 2 days. The $3^{rd}$ 30 minute session could be delivered after 4 days. Finally, the $4^{th}$ 30 minute session could be delivered for all subsequent sessions after 7 days.

If a triggered session is delivered completely, it advances the therapy schedule to the next table entry.

Another enhancement is that the initial set amplitude only takes effect if the subsequent triggered session is completely delivered. If the first session is aborted by a magnet application, the device reverts to a Shelf Mode. In this way, the first session is always a triggered session that occurs in the clinician setting.

Finally, the amplitude and place in the session table are saved in non-volatile memory when they change. This avoids a resetting of the therapy schedule and need to reprogram the amplitude in the event of a device reset.

By way of example, one preferred set of parameters to use to define a stimulation regimen is: T1=0.5 milliseconds, T2=500 milliseconds, T3=30 minutes, T4=7 days (10,080 minutes, and A1=15 volts (across 1 kOhm), or 15 milliamperes (mA).

It is to be emphasized that the values shown above for the stimulation regimen are representative of only one preferred stimulation regimen that could be used.

It is also emphasized that the ranges of values presented in the claims for the parameters used with the invention have been selected after many months of careful research and study, and are not arbitrary. For example, the ratio of T3/T4, which sets the duty cycle, has been carefully selected to be very low, e.g., no more than 0.05. Maintaining a low duty cycle of this magnitude represents a significant change over what others have attempted in the implantable stimulator art. Not only does a very low duty cycle allow the battery itself to be small (coin cell size), which in turn allows the IEAD housing to be very small, which makes the IEAD ideally suited for being used without leads, thereby making it relatively easy to implant the device at the desired stimulation site (e.g., acupoint), but it also limits the frequency and duration of stimulation sessions.

Limiting the frequency and duration of the stimulation sessions is a key aspect of Applicant's invention because it recognizes that some treatments, such as treating overweight conditions, are best done slowly and methodically, over time, rather than quickly and harshly using large doses of stimulation (or other treatments) aimed at forcing a rapid change in the patient's condition. Moreover, applying treatments slowly and methodically is more in keeping with traditional acupuncture methods (which, as indicated previously, are based on over 2500 years of experience). In addition, this slow and methodical conditioning is consistent with the time scale for remodeling of the central nervous system needed to produce a sustained therapeutic effect. Thus, Applicant has based its treatment regimen on the slow-and-methodical approach, as opposed to the immediate-and-forced approach adopted by many, if not most, prior art implantable electrical stimulators.

Once the stimulation regimen has been defined and the parameters associated with it have been pre-set into the memory of the micro-controller circuit U2, the IEAD 100 needs to be implanted. Implantation is usually a simple procedure, and is described above in connection, e.g., with the description of FIGS. 1A and 1B.

Figure 16:
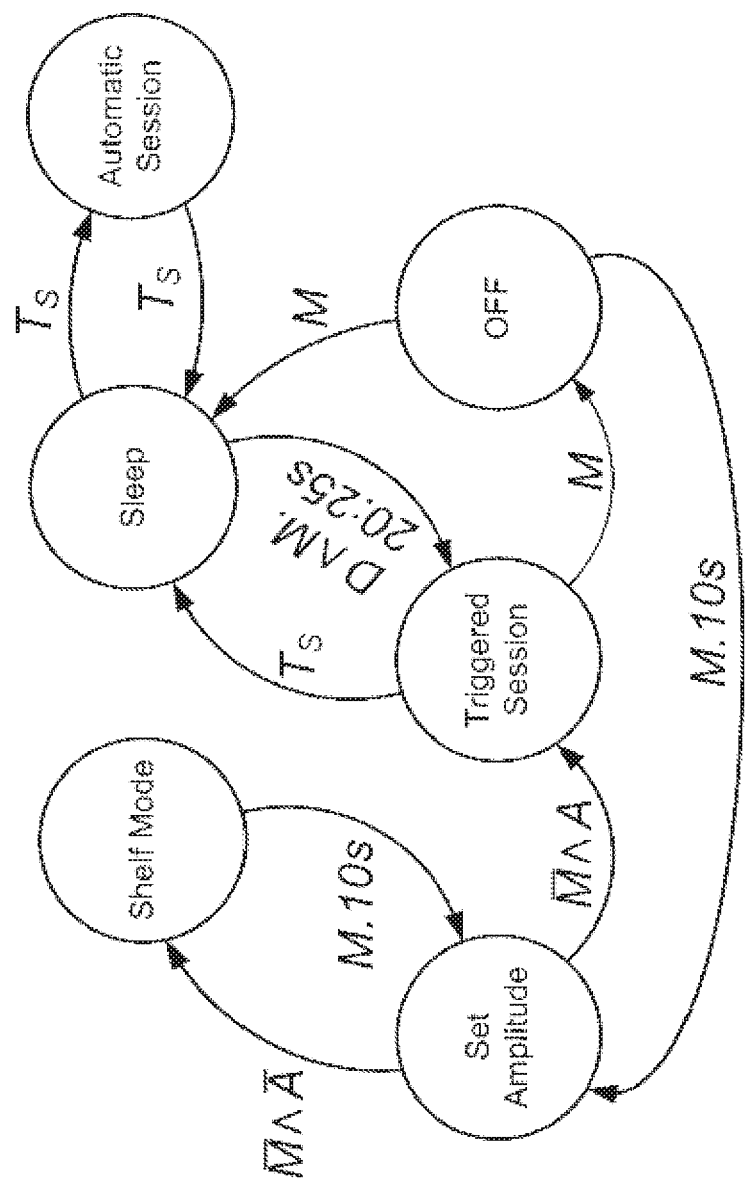
FIG. 16 shows a state diagram that depicts the various states the IEAD may assume as controlled by an external magnet.

After implantation, the IEAD must be turned ON, and otherwise controlled, so that the desired stimulation regimen or stimulation paradigm may be carried out. In one preferred embodiment, control of the IEAD after implantation, as well as anytime after the housing of the IEAD has been hermetically sealed, is performed as shown in the state diagram of FIG. 16. Each circle shown in FIG. 16 represents an operating "state" of the micro-controller U2 (FIG. 13A or 14). As seen in FIG. 16, the controller U2 only operates in one of six states: (1) a "Set Amplitude" state, (2) a "Shelf Mode" state, (3) a "Triggered Session" state, (4) a "Sleep" state, (5) an "OFF" state, and an (6) "Automatic Session" state. The "Automatic Session" state is the state that automatically carries out the stimulation regimen using the pre-programmed parameters that define the stimulation regimen.

Shelf Mode is a low power state in which the IEAD is placed prior to shipment. After implant, commands are made through magnet application. Magnet application means an external magnet, typically a small hand-held cylindrical magnet, is placed over the location where the IEAD has been implanted. With a magnet in that location, the magnetic sensor U4 senses the presence of the magnet and notifies the controller U2 of the magnet's presence.

From the "Shelf Mode" state, a magnet application for 10 seconds (M.10 s) puts the IEAD in the "Set Amplitude" state. While in the "Set Amplitude" state, the stimulation starts running by generating pulses at zero amplitude, incrementing every five seconds until the patient indicates that a comfortable level has been reached. At that time, the magnet is removed to set the amplitude.

If the magnet is removed and the amplitude is non-zero ($\overline{M}/\mathrm{A}$), the device continues into the "Triggered Session" so the patient receives the initial therapy. If the magnet is removed during "Set Amplitude" while the amplitude is zero ($\overline{M}/\overline{A}$), the device returns to the Shelf Mode.

The Triggered Session ends and stimulation stops after the session time ($T_S$) has elapsed and the device enters the "Sleep" state. If a magnet is applied during a Triggered Session (M), the session aborts to the "OFF" state. If the magnet remains held on for 10 seconds (M.10 s) while in the "OFF" state, the "Set Amplitude" state is entered with the stimulation level starting from zero amplitude as described.

If the magnet is removed ($\overline{M}$) within 10 seconds while in the OFF state, the device enters the Sleep state. From the Sleep state, the device automatically enters the Automatic Session state when the session interval time has expired ($T_I$). The Automatic Session delivers stimulation for the session time ($T_S$) and the device returns to the Sleep state. In this embodiment, the magnet has no effect once the Automatic Session starts so that the full therapy session is delivered.

While in the Sleep state, if a magnet has not been applied in the last 30 seconds (D) and a magnet is applied for a window between 20-25 seconds and then removed (M.20: 25 s), a Triggered Session is started. If the magnet window is missed (i.e. magnet removed too soon or too late), the 30 second de-bounce period (D) is started. When de-bounce is active, no magnet must be detected for 30 seconds before a Triggered Session can be initiated.

The session interval timer runs while the device is in Sleep state. The session interval timer is initialized when the device is woken up from Shelf Mode and is reset after each session is completely delivered. Thus abort of a triggered session by magnet application will not reset the timer, the Triggered Session must be completely delivered.

The circuitry that sets the various states shown in FIG. 16 as a function of externally-generated magnetic control commands, or other externally-generated command signals, is the micro-controller U2 (FIG. 14), the processor U2 (FIG. 13A), or the control circuit 220 (FIGS. 10, 11 and 12). Such processor-type circuits are programmable circuits that operate as directed by a program. The program is often referred to as "code", or a sequence of steps that the processor circuit follows. The "code" can take many forms, and be written in many different languages and formats, known to those of skill in the art. Representative "code" for the micro-controller U2 (FIG. 14) for controlling the states of the IEAD as shown in FIG. 16 is found in Appendix C.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense and are not intended to be exhaustive or to limit the invention to any precise form disclosed. Many modifications and variations are possible in light of the above teaching. Thus, while the invention(s) herein disclosed has been described by means of specific embodiments and applications thereof, numerous modifications and variations could be made thereto by those skilled in the art without departing from the scope of the invention(s) set forth in the claims.

What is claimed is:

1. An implantable electroacupuncture device for treating a medical condition of a patient through application of electroacupuncture stimulation pulses to a target tissue location within the patient, comprising:
    a housing configured to be implanted beneath a skin surface of the patient and having a first surface adapted to face inwardly into tissue of the patient at or near the target tissue location;
    pulse generation circuitry located within the housing and electrically coupled to at least two electrodes, the pulse generation circuitry being adapted to deliver stimulation sessions by way of the at least two electrodes to the target tissue location in accordance with a stimulation regimen, the stimulation sessions each including a plurality of the electroacupuncture stimulation pulses, the stimulation regimen requiring that each stimulation session included in the stimulation sessions have a duration of T3 minutes and a rate of occurrence of once every T4 minutes, wherein a ratio of T3 to T4 is no greater than 0.05; and
    a primary battery contained within the housing and electrically coupled to the pulse generation circuitry, the primary battery having an internal impedance greater than 5 ohms and a capacity of less than 60 mAh, wherein the primary battery is the only battery that provides power to the pulse generation circuitry.

2. The implantable electroacupuncture device of claim 1, wherein the at least two electrodes are located on the first surface.

3. The implantable electroacupuncture device of claim 2, wherein the at least two electrodes comprise:
    a central electrode located substantially in a center of the first surface of the housing; and
    a circumferential electrode located substantially around and at least 5 mm distant from a center of the central electrode.

4. The implantable electroacupuncture device of claim 3, wherein the circumferential electrode is an anode electrode and the central electrode is a cathode electrode.

5. The implantable electroacupuncture device of claim 3, wherein the circumferential electrode is a cathode electrode and the central electrode is an anode electrode.

6. The implantable electroacupuncture device of claim 3, wherein the circumferential electrode comprises a ring electrode attached around a perimeter edge of the housing.

7. The implantable electroacupuncture device of claim 1, wherein the at least two electrodes are located on a lead that is attached to the implantable electroacupuncture device.

8. The implantable electroacupuncture device of claim 1, wherein the housing is coin-shaped having a diameter no greater than about 25 mm and a thickness of no greater than about 2.5 mm.

9. The implantable electroacupuncture device of claim 1, wherein the primary battery has sufficient capacity to power the pulse generation circuitry in accordance with the stimulation regimen for a minimum of 2 years.

10. The implantable electroacupuncture device of claim 1, wherein the primary battery has a nominal output voltage of 3 volts.

11. The implantable electroacupuncture device of claim 10, wherein the pulse generation circuitry includes:
    a boost converter circuit that boosts the nominal voltage of the primary battery to an output voltage VOUT that is at least three times a nominal battery voltage;
    means for selectively turning the boost converter circuit OFF and ON to limit the amount of current that may be drawn from the primary battery; and
    an output circuit powered by VOUT that generates the stimulation sessions as defined by the stimulation regimen.

12. The implantable electroacupuncture device of claim 11, wherein the means for selectively turning the boost converter circuit OFF and ON comprises a control circuit configured to generate a digital signal that modulates the boost converter circuit between an OFF state and an ON state, with the ON state comprising no more than about 2% of the time that the implantable electroacupuncture device is operating.

13. The implantable electroacupuncture device of claim 11, wherein the means for selectively turning the boost converter circuit OFF and ON comprises a boost converter circuit having a shut down feature which automatically places the boost converter circuit in an OFF state whenever a battery voltage of the primary battery falls below a set minimum value, wherein the set minimum value of the primary battery below which the boost converter is placed in an OFF state comprises a voltage that is sufficiently high to continue to power other digital processing circuits within the pulse generation circuitry even when the boost converter is turned OFF.

14. The implantable electroacupuncture device of claim 11, wherein the pulse generation circuitry further includes means for reducing leading edge transient signals that may be present in the stimulation pulses generated by the pulse generation circuitry.

15. The implantable electroacupuncture device of claim 14, wherein the output circuit of the pulse generation circuitry includes a programmable current source, and wherein the means for reducing leading edge transient signals comprises a cascode circuit at the input of the programmable current source.

16. The implantable electroacupuncture device of claim 15, wherein the pulse generation circuitry further includes means for kick starting the programmable current source when low amplitude stimulation pulses are generated, wherein such kick starting eliminates or reduces undesired delays in the leading edge of the stimulation pulses generated by the pulse generation circuitry.

17. The implantable electroacupuncture device of claim 1, wherein the electronic circuitry includes power management circuitry that limits an amount of instantaneous current that can be drawn from the primary battery.

18. The implantable electroacupuncture device of claim 1, further comprising a sensor contained within the housing responsive to operating commands wirelessly communicated to the implantable electroacupuncture device from a non-implanted location, the operating commands allowing limited external control of the implantable electroacupuncture device.

19. The implantable electroacupuncture device of claim 1, wherein a second surface of the housing, on an opposite side of the housing from the first surface, when implanted, is adapted to be closest to the patient's skin.

20. The implantable electroacupuncture device of claim 1, wherein, during each stimulation session, stimulation pulses having a specified width and a specified amplitude are generated at a specified rate.

* * * * *